US009658181B2

(12) United States Patent
Balasubramanian et al.

(10) Patent No.: US 9,658,181 B2
(45) Date of Patent: May 23, 2017

(54) WHOLE BLOOD HEMOLYSIS SENSOR

(71) Applicant: Instrumentation Laboratory Company, Bedford, MA (US)

(72) Inventors: Shankar Balasubramanian, Acton, MA (US); Paul D'Orazio, Boxborough, MA (US)

(73) Assignee: Instrumentation Laboratory Company, Bedford, MA (US)

( * ) Notice: Subject to any disclaimer, the term of this patent is extended or adjusted under 35 U.S.C. 154(b) by 340 days.

(21) Appl. No.: 14/202,398

(22) Filed: Mar. 10, 2014

(65) Prior Publication Data
US 2014/0262831 A1    Sep. 18, 2014

Related U.S. Application Data

(60) Provisional application No. 61/782,166, filed on Mar. 14, 2013.

(51) Int. Cl.
*G01N 27/327* (2006.01)
*C12Q 1/26* (2006.01)
*C12Q 1/00* (2006.01)

(52) U.S. Cl.
CPC ....... *G01N 27/327* (2013.01); *G01N 27/3271* (2013.01); *C12Q 1/001* (2013.01); *C12Q 1/26* (2013.01); *G01N 27/3277* (2013.01)

(58) Field of Classification Search
CPC .. G01N 27/327–27/3278; G01N 27/40; C12Q 1/00–1/003
USPC .... 204/403.01–403.15; 205/777.5, 779, 778, 205/792, 793
See application file for complete search history.

(56) References Cited

U.S. PATENT DOCUMENTS

| | | | |
|---|---|---|---|
| 5,416,026 A * | 5/1995 | Davis | G01N 33/725 436/169 |
| 5,593,638 A | 1/1997 | Davis | |
| 6,485,923 B1 | 11/2002 | Yani et al. | |
| 6,615,078 B1 | 9/2003 | Burson et al. | |
| 6,632,349 B1 | 10/2003 | Hodges et al. | |

(Continued)

FOREIGN PATENT DOCUMENTS

| | | |
|---|---|---|
| EP | 2151682 | 2/2010 |
| EP | 2 050 824 | 8/2010 |

(Continued)

OTHER PUBLICATIONS

Blankman et al., "Direct Voltammetric Investigation of the Electrochemical Properties of Human Hemoglobin: Relevance to Physiological Redox Chemistry," *Biochemistry*, 39:14806-14812 (2000).

(Continued)

*Primary Examiner* — Bach Dinh
(74) *Attorney, Agent, or Firm* — Burns & Levinson, LLP

(57) ABSTRACT

The present invention pertains to a hemolysis sensor, a hemolysis sensor system and methods of utilizing the hemolysis sensor or hemolysis sensor system to monitor or detect hemolysis in a sample, such as a whole blood sample, a plasma sample, a serum sample or hemolyzed blood. The hemolysis sensor responds to extracellular hemoglobin levels, for example, extracellular hemoglobin in a whole blood sample as a method for detecting hemolysis in whole blood.

16 Claims, 13 Drawing Sheets

(56) References Cited

U.S. PATENT DOCUMENTS

| | | | |
|---|---|---|---|
| 6,960,466 B2* | 11/2005 | Pamidi | C12Q 1/002 435/14 |
| 6,998,248 B2 | 2/2006 | Yani et al. | |
| 7,749,764 B2 | 7/2010 | Su et al. | |
| 7,790,464 B2 | 9/2010 | Tarasev | |
| 9,388,503 B2 | 7/2016 | Pamidi et al. | |
| 2002/0012952 A1 | 1/2002 | Murthy et al. | |
| 2003/0201177 A1 | 10/2003 | Hodges et al. | |
| 2010/0267048 A1 | 10/2010 | Tanaka et al. | |
| 2010/0299072 A1* | 11/2010 | Kamata | G01N 33/5438 702/19 |
| 2012/0152764 A1 | 6/2012 | Lin et al. | |

FOREIGN PATENT DOCUMENTS

| | | |
|---|---|---|
| JP | 2005/034132 | 2/2005 |
| WO | 00/51655 | 9/2000 |
| WO | 02/097419 | 12/2002 |
| WO | 2009/140343 | 11/2009 |
| WO | 2010/055306 | 5/2010 |

OTHER PUBLICATIONS

Brett et al., "Poly(methylene blue) modified electrode sensor for haemoglobin," *Analytica Chimica Acta*, 385:119-123 (1999).

Chen et al., "Electrochemical Determination of Human Hemoglobin by Using Ferrocene Carboxylic Acid Modified Carbon Powder Microelectrode," *Analytical Letters*, 36(9):2049-2059 (2003).

Hsieh et al., "Comparison of an electrochemical biosensor with optical devices for hemoglobin measurement in human whole blood samples," *Clinica Chimica Acta*, 412:2150-2156 (2011).

Li et al, "Silver Nanoparticles Modified Electrode and Its Application to the Determination of Hemoglabin," *Analytical Chemistry*, 34(1):31-34 (2006) (Article is in Chinese).

Li et al, "Silver Nanoparticles Modified Electrode and Its Application to the Determination of Hemoglabin," *Analytical Chemistry*, 34(1):31-34 (2006) (English Abstract of C5).

Liu et al., "Carbon-Nanotube-Enhanced Direct Electron-Transfer Reactivity of Hemoglobin Immobilized on Polyurethane Elastomer Film," *J. Phys. Chem. B*, 111:1182-1188 (2007).

Zhao et al., "Fabrication, characterization of $Fe_3O_4$ multilayer film and its application in promoting direct electron transfer of hemoglobin," *Eletrochemistry Communications*, 8:148-154 (2006).

Patent Examination Report No. 1 issued in counterpart Australian patent application No. 2014241111 on Jun. 2, 2016 (3 pages).

International Preliminary Report on Patentability for International Application No. PCT/US2014/022447, dated Sep. 24, 2015 (6 pages).

International Search Report and Written Opinion for International Application No. PCT/US2014/022447, mailed on Jul. 11, 2014, 10 pages.

Kobos et al., "Electrochemical Determination of Hemoglobin, Hematocrit, and Hemolysis," Clinical Chemistry 33(1):153-158 (1987).

Office Action from related Japanese Application No. 2016-500970, dated Nov. 22, 2016.

English translation of Office Action from related Japanese Application No. 2016-500970, dated Nov. 22, 2016.

Office Action from related Chinese Application No. 2014800234036, dated Oct. 27, 2016.

Englis translation of Office Action from related Chinese Application No. 2014800234036, dated Oct. 27, 2016.

\* cited by examiner

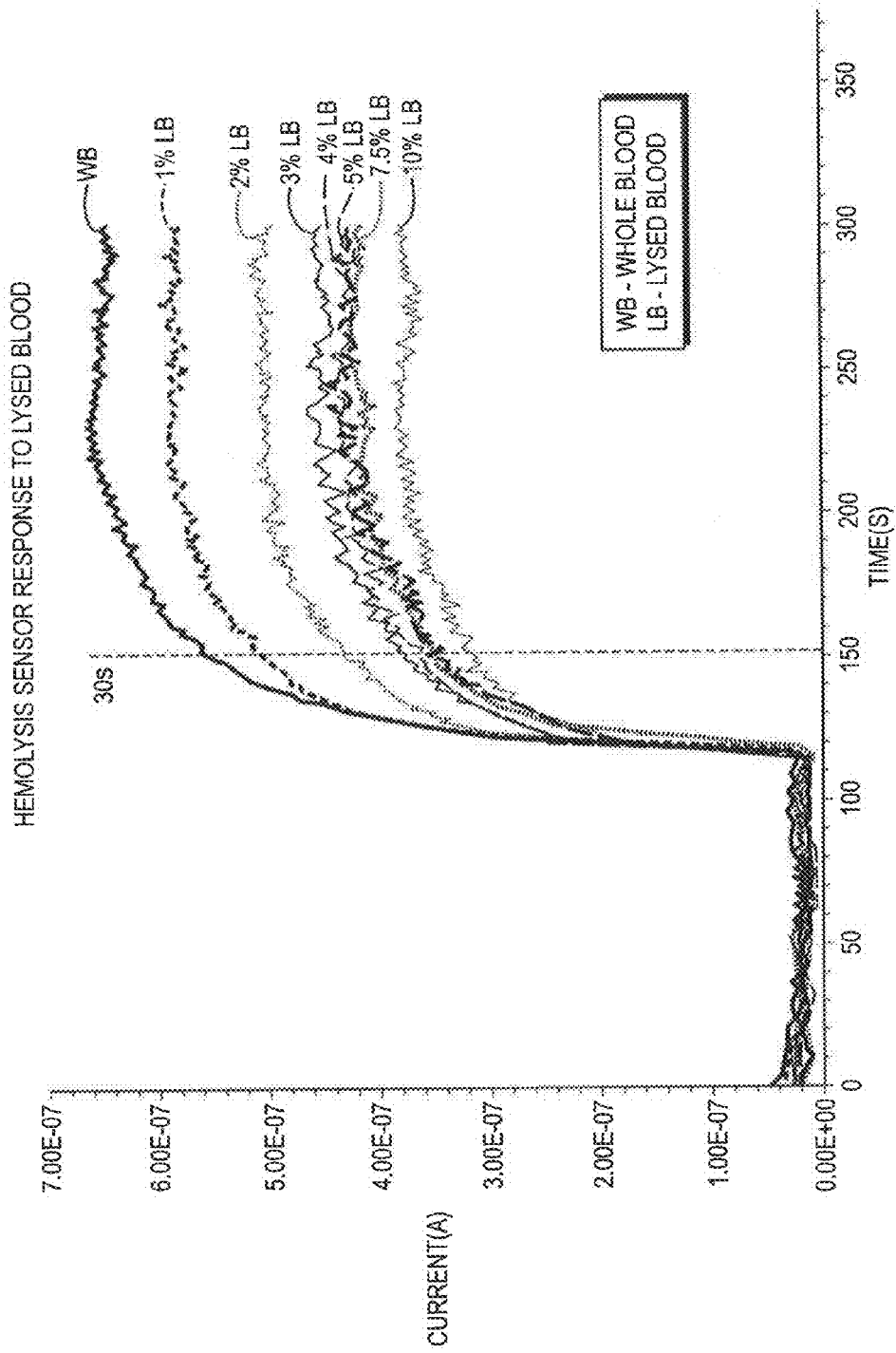

WHOLE BLOOD HEMOLYSIS SENSOR

CROSS REFERENCE TO RELATED APPLICATION

This application claims priority to and benefit of U.S. Provisional Application No. 61/782,166, filed Mar. 14, 2013, the entire contents of which are incorporated by reference herein for all purposes.

TECHNICAL FIELD OF THE INVENTION

The present invention pertains to a hemolysis sensor, a hemolysis sensor system and methods of utilizing the hemolysis sensor or hemolysis sensor system to monitor or detect hemolysis in a sample, such as a whole blood sample, a plasma sample, a serum sample or hemolyzed blood sample, and assess the contribution of hemolysis to levels of electrolytes, e.g., potassium, in the sample.

BACKGROUND

The concentration of analytes in whole blood, meaning the combined cellular and fluid portion of blood, may differ significantly in amount from the concentration of analytes found within red blood cells. For example, in whole blood, potassium levels are usually about 4.0 mM, while potassium concentration with in red blood cells is usually about 150 mM.

In the course of collecting and handling whole blood from a patient, some cells, red blood cells in particular, may be physically damaged causing rupture of the red blood cell. The phenomenon of ruptured red blood cells is known as "hemolysis". When hemolysis occurs in a whole blood sample, the contents of the red blood cells is intermixed with the contents of the cell-free portion of whole blood, termed plasma, or in some cases, serum. Hemoglobin, a constituent of whole blood normally found within red blood cells and not free in the fluid portion of blood, and other intracellular elements, e.g., potassium are released from the intracellular compartment of red blood cells into the fluid portion of blood, i.e. plasma or serum.

Because the concentration of potassium within red blood cells is 25-75 times higher than the concentration of potassium in normal plasma, measuring potassium in the fluid portion of a patient's hemolyzed blood sample will induce an artifact, such as an artificial measured elevation of the patient's actual plasma potassium level. The potassium concentration in the fluid portion of non-hemolyzed blood is an important indicator of numerous conditions. An over estimate of the concentration of potassium in hemolyzed blood may result in treatment of the patient for hyperkalemia (increased blood potassium) when the patient may actually have low concentration of potassium in the patient's non-hemolyzed blood sample. Unfortunately, only a relatively small number of ruptured red blood cells can result in an artificially elevated blood potassium level.

In addition to elevated plasma potassium when a blood sample is hemolyzed, other analytes such as lactate dehydrogenase, acid phosphatase, aspartate aminotransferase, and alanine aminotransferase, for example, are also present in higher concentration in red blood cells than in the fluid portion of blood, and these analytes may be artificially elevated in hemolyzed blood.

Current methods for detecting hemolysis in a patient's blood sample include centrifuging the blood sample to remove blood cells, then by optical methods, determining the presence of hemoglobin in the plasma portion. Hemoglobin imparts a pink or red color to plasma when the color ordinarily in a non-hemolyzed blood sample is slightly yellow. No current methods operate on whole, non filtered or non-centrifuged blood to determine hemolysis.

SUMMARY OF THE INVENTION

In one aspect, the invention provides an electrochemical sensor system for detecting hemolysis in a whole blood sample comprising an electrochemical hemolysis sensor having an outer membrane comprising a thickness in the range of about 0.1 to about 50 μm for enhancing efflux of hydrogen peroxide ($H_2O_2$), another membrane comprising a hydrogen peroxide generating oxidoreductase enzyme and a reagentless flow chamber positioned adjacent to the outer membrane for contacting the whole blood sample with the outer membrane of the sensor. The outer membrane thickness is adapted to enhance efflux of hydrogen peroxide. In one embodiment, the outer membrane comprises a hydrogel comprising a water content ranging from about 0.1% to about 100%. In one embodiment, the oxidoreductase enzyme comprises a glucose oxidase, or a lactate oxidase, or a mixture of enzymes comprising a creatininase and/or creatinase and a sarcosine oxidase.

In another aspect, the invention provides a method for detecting hemolysis in a whole blood sample comprising introducing the whole blood sample to an electrochemical sensor. The electrochemical sensor comprises a plurality of membranes or layers. In the plurality of membranes of the electrochemical sensor one of the plurality of membranes comprises an intermediate layer comprising an oxidoreductase enzyme or a mixture of enzymes that function as an oxidoreductase capable of generating hydrogen peroxide. Another one of the plurality of membranes comprises an outer membrane that contacts the blood sample and which is permeable to and enhances the efflux of hydrogen peroxide. Yet, another one of the plurality of membranes comprises an inner membrane. The introduction of the whole blood sample into the electrochemical hemolysis sensor is followed by detecting an electrochemical signal generated by hydrogen peroxide in the presence of Hb ($Fe^{2+}$), wherein a decrease of detectable electrical current in the range of 4% to 50% compared to a non-hemolyzed whole blood sample, is indicative of hemolysis in the whole blood sample. The oxidoreductase enzyme comprises a glucose oxidase, or a lactate oxidase, or a mixture of enzymes comprising a creatininase and/or creatinase and a sarcosine oxidase.

In another aspect, the invention provides a method for determining whether an elevated level of an analyte in a whole blood sample of a patient is an artifact related to hemolysis. The method comprises introducing the whole blood sample from the patient to the electrochemical hemolysis sensor described herein. The hemolysis sensor comprises an oxidoreductase enzyme capable of generating hydrogen peroxide. The hemolysis sensor also comprises an outer membrane comprising a thickness in a range of about 0.1 μm to about 50 μm. The thickness of the outer membrane is adapted to enhance efflux of hydrogen peroxide. After introducing the whole blood sample to the electrochemical sensor, an electrochemical signal generated by hydrogen peroxide in the presence of hemoglobin (Hb ($Fe^{2+}$)) is detected. A decrease of a detectable electrical current in a range of about 4% to about 50% compared to a standard non-hemolyzed whole blood sample is indicative of the hemolysis as the cause of the elevated level of the analyte in the whole blood sample of the patient.

BRIEF DESCRIPTION OF THE DRAWING

In FIG. 7, the x-axis represents time in seconds and the y-axis represents current in ampere.

In FIG. 8A, the x-axis represents time in seconds and the y-axis represents current in ampere.

In FIG. 8B, the x-axis represents plasma hemoglobin (g/dL) and the y-axis represents current in nanoampere.

FIG. 9A is a graph illustrating a real-time current profile generated by an exemplary hemolysis sensor according to the invention for the whole and the hemolyzed blood samples. In FIG. 9A, the x-axis represents time in seconds and the y-axis represents current in ampere.

In FIG. 9B, the x-axis represents lysed blood (% vol/vol) and the y-axis represents current in nanoampere In FIG. 9C, the x-axis represents lysed blood (% vol/vol) and the y-axis represents current in nano ampere.

In FIG. 10, the x-axis represents partial oxygen pressure ($pO_2$) in mmHg and the y-axis represents current in ampere.

DESCRIPTION OF THE INVENTION

Figure 1:
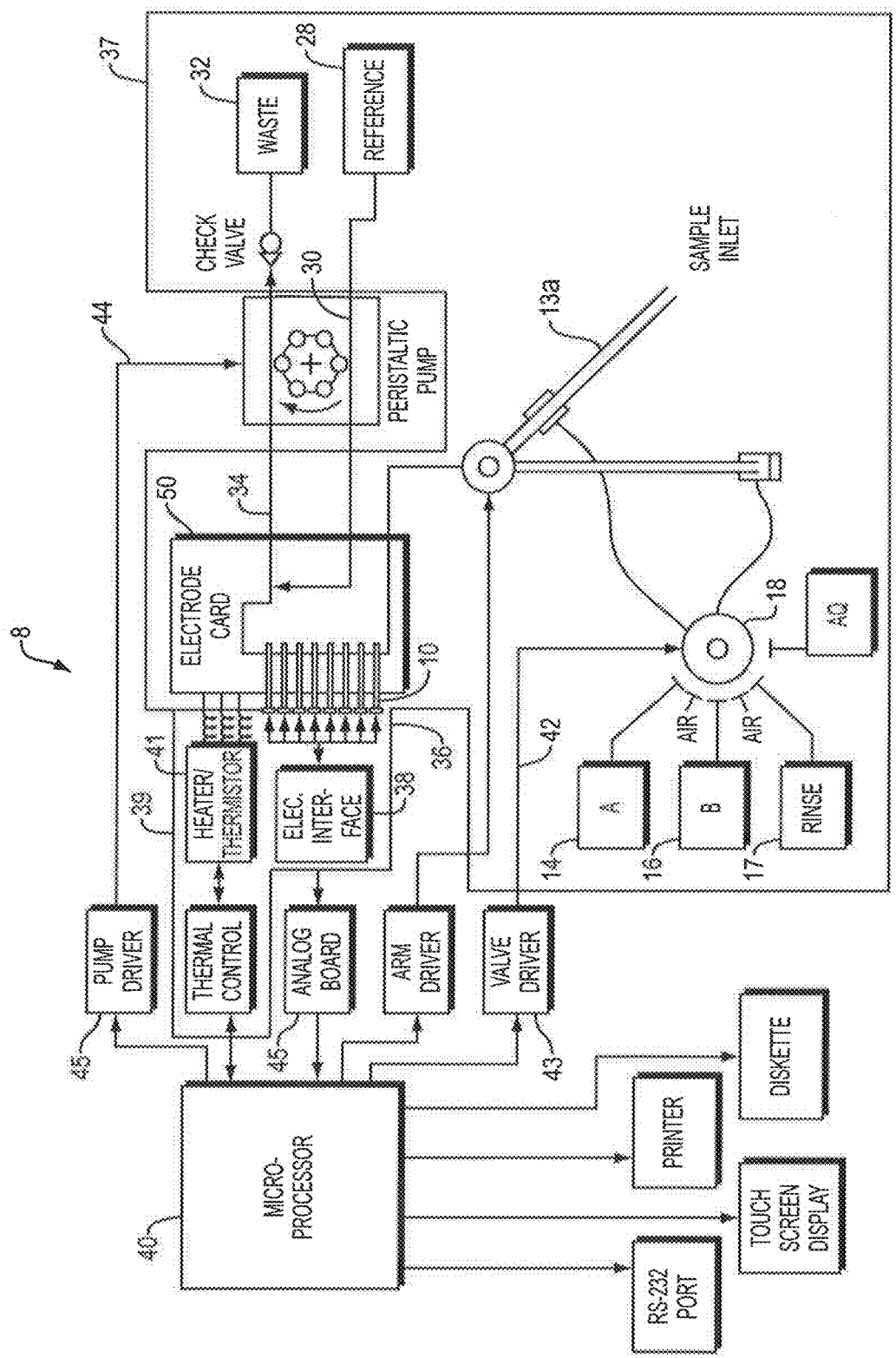
FIG. 1 illustrates an exemplary electrochemical sensor system encompassing an exemplary sensor card and a bank of sensors in a sensor assembly, including a hemolysis sensor (illustrated in FIG. 2), according to an embodiment of the invention.

The present invention pertains to a hemolysis sensor, a hemolysis sensor system and methods of utilizing the hemolysis sensor or hemolysis sensor system to monitor or detect hemolysis in a sample, such as a whole blood sample, a plasma sample, a serum sample, or hemolyzed blood and to assess the contribution of hemolysis to levels of analytes, e.g., potassium in the blood sample.

Briefly, a hemolysis sensor and method for detecting hemolysis, described herein, takes advantage of membrane permeability to $H_2O_2$. Membrane permeability, as used herein, refers to the quality, described in greater detail below, of a membrane (e.g., an outer membrane of the hemolysis sensor) of the hemolysis sensor to readily allow hydrogen peroxide to pass in and out of the membrane. Membrane permeability, as used herein, may be adjusted, for example, by the water content of the outer membrane of the hemolysis sensor. A membrane with higher water content has greater permeability for hydrogen peroxide compared to a membrane with lower water content. The membrane water content for the hemolysis sensor according to the invention is preferably in the range of about 30 to 100%.

Membrane permeability, as used herein, also includes selective membrane permeability. For example, an interference rejection membrane in the hemolysis sensor selectively permits hydrogen peroxide to readily pass through the membrane while acting as a barrier against the permeability of other substances, e.g., interfering substances. Selective membrane permeability, as used herein also includes the ability of one or more hemolysis sensor membranes (e.g., the outer membrane) to allow some particles to pass freely (e.g., hydrogen peroxide) through the membrane while retarding or completely preventing the passage of other substances, for example, a protein molecule from the whole blood sample.

According to one embodiment of the invention, the hemolysis sensor takes advantage of the peroxidase-like activity of extracellular hemoglobin (henceforth referred to as "hemoglobin", unless specifically described, otherwise) in a whole blood sample. Hydrogen peroxide ($H_2O_2$) is produced from a substrate (e.g., blood glucose) when the substrate (e.g., blood glucose) reacts with an oxidoreductase enzyme (e.g., glucose oxidase) in the presence of a gas (e.g., oxygen) and the $H_2O_2$ is scavenged by extracellular hemoglobin present in the fluid portion of the whole blood sample.

"Scavenged", as used herein, refers to decomposition or break down of $H_2O_2$ into smaller components by hemoglobin when $H_2O_2$ comes in contact with hemoglobin in the hemolysis sensor.

Hemoglobin-induced decomposition or breaking down of hydrogen peroxide into smaller components generates a hydrogen peroxide diffusion gradient in the hemolysis sensor causing hydrogen peroxide to preferably diffuse from a membrane of the hemolysis sensor that generates hydrogen peroxide, e.g., the intermediate enzyme membrane, described in greater detail below, through and to the outer surface of the outer membrane, which is in contact with extracellular hemoglobin in the blood sample introduced into the hemolysis sensor.

The scavenging action of hemoglobin in the hemolysis sensor decreases the $H_2O_2$ availability needed for oxidation at the working electrode, e.g., a platinum electrode, as compared to when hemoglobin is absent in the hemolysis sensor. Hence, in the presence of hemoglobin in the hemolysis sensor, less current is generated by the working electrode as compared to a blood sample that is not hemolyzed.

It is important to note that only the extracellular hemoglobin (outside the red blood cells) in plasma or serum reacts with hydrogen peroxide and produces signal for hemolysis. Hemoglobin inside the red blood cell has no effect on the hemolysis sensor.

In another embodiment of the invention, the hemolysis sensor, according to the invention, is useful for assessing whether or not an increase in the concentration of various analytes in a patient's blood sample, for example, potassium, creatinine or magnesium which have greater intracellular concentrations than the concentration of the same analytes in the fluid portion of the whole blood, is due to hemolysis in the blood sample, i.e., loss of the integrity of red blood cells or due to some physiological abnormality in the patient from whom the blood sample was taken. Table 1 below is illustrative of the effect of lysed red blood cells on the extracellular concentration of potassium, an analyte which has a high intracellular concentration in intact red blood cells.

TABLE 1

| Lysed blood, % (v/v) | $K^+$, mmol/L |
| --- | --- |
| 0 | 3.9 |
| 1 | 4.7 |
| 2 | 5.3 |
| 3 | 6.1 |
| 4 | 6.8 |
| 5 | 7.5 |
| 7.5 | 9 |
| 10 | 10.8 |

Whether an increase in analyte levels in whole blood, such as potassium, is due to hemolysis of the whole blood sample or to other unspecified causes which may require other therapy may be determined by the hemolysis sensor according to the invention.

Accordingly, hemolysis of a whole blood sample may be correlated with alterations, typically an increase in the concentration of analytes such as potassium, creatinine or magnesium, in a whole blood sample. Thus, in one aspect, the invention is directed to a hemolysis sensor or hemolysis sensor system for detecting the presence of extracellular hemoglobin in the presence of the cellular elements of a whole blood sample, and correlating increased extracellular levels of analytes in a blood sample, preferably a whole blood sample, with hemolysis in the blood sample.

Generally, the hemolysis sensor described herein is a component, such as a replacement component, of an exemplary electrochemical system 8, shown in FIG. 1, described below in greater detail.

Electrochemical Sensor System

Figure 2:
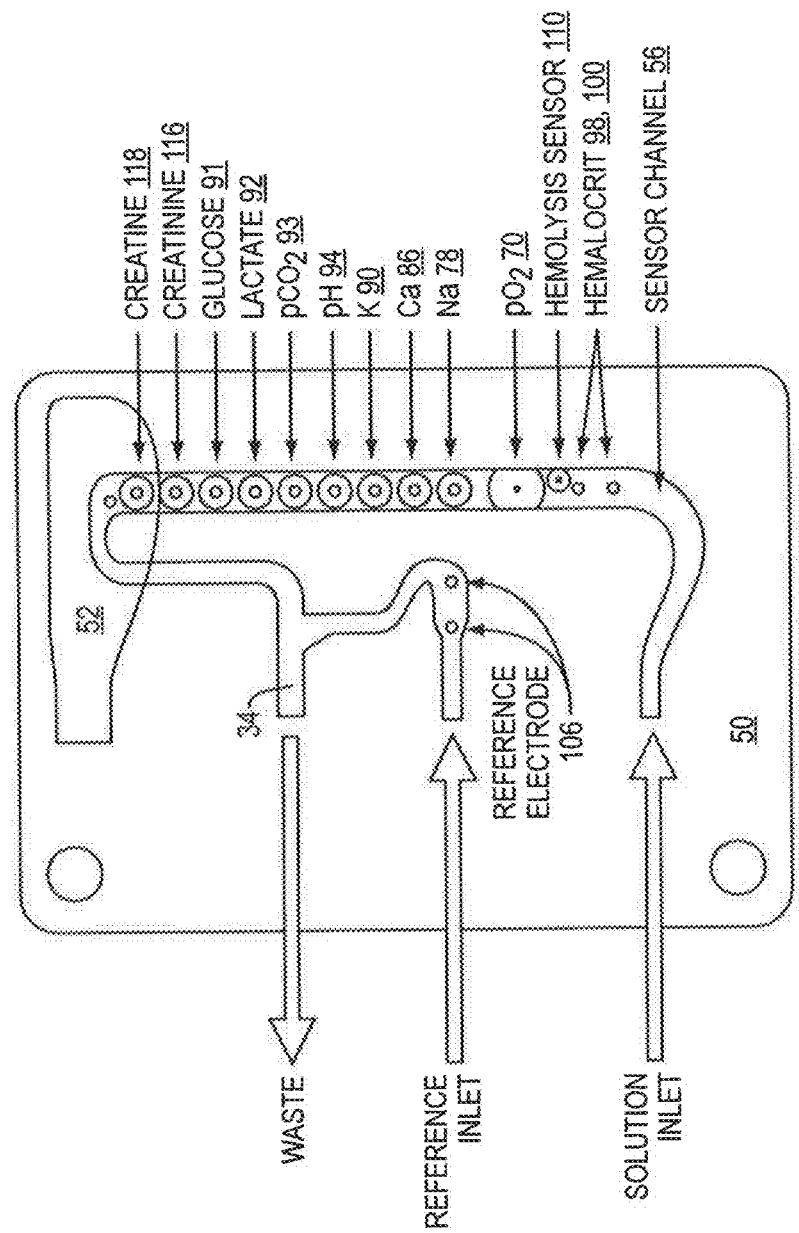
FIG. 2 illustrates a reverse frontal view of the exemplary sensor card including the hemolysis sensor in the bank of sensors in the sensor assembly, illustrated in FIG. 1, according to an embodiment of the invention.

Referring to FIG. 1, in one embodiment according to the invention, an electrochemical sensor system 8 employs a sensor assembly, generally indicated at 10, incorporating a plurality of electrodes, including a hemolysis sensor 110, illustrated in FIG. 2, adapted to make electrical measurements on a sample, such as a blood sample, e.g., a whole blood sample, introduced to the sensor assembly 10. Other electrodes in the plurality of electrodes may include one or more of, glucose 91, lactate 92, creatine 118, creatinine 116, $pCO_2$ 93, pH 94, $K^+$ 90, $Ca^{++}$ 86, $Na^+$ 78, and $pO_2$ 70. Whole blood samples to be analyzed by the system 8 are directed to an outer surface 200 of an outer membrane 51, discussed below in greater detail below, of the hemolysis sensor 110. In one embodiment of the invention, blood samples, e.g., whole blood to be analyzed by the system 8 are introduced through a sample inlet 13a. Blood samples are obtained by, for example, a syringe, a tube, by an evacuated tube system, by venipuncture, by phlebotomy or are derived on a periodic basis from an extracorporeal blood flow circuit connected to a patient during, for example, open heart surgery. Whole blood samples are introduced into a sensor channel 56 in contact with an outer surface 200 of an outer membrane 51, via the sample inlet 13a or through other automatic means, or manually, such as by syringe. Alternatively, the whole blood samples may be introduced as discrete samples, as illustrated in FIG. 2. Whole blood samples are not subjected to centrifugation at all prior to or during analysis of the whole blood sample for hemolysis in the hemolysis sensor 110.

Referring to FIG. 2, in one embodiment of the invention, the hemolysis sensor 110 comprises a reagentless chamber, for example, the sensor channel 56. The reagentless chamber 56 is advantageous because the hemolysis sensor 110 does not require a colorimetric reagent or other reagent added to the whole blood sample to measure hemoglobin prior to or during the analysis of the whole blood for hemolysis in the hemolysis sensor 110.

With continued reference to FIG. 1 and FIG. 2, in one embodiment of the invention, the electrochemical system 8 includes a disposable cartridge 37 (FIG. 1). The cartridge 37 incorporates a sensor assembly 10 including a plurality of sensors (illustrated in FIG. 2), including a hemolysis sensor 110, adapted to make electrical measurements on a sample, such as a blood sample, e.g., a whole blood sample, introduced to the sensor assembly 10. Other electrodes in the plurality of sensors may include one or more of, glucose 91, lactate 92, creatine 118, creatinine 116, $pCO_2$ 93, pH 94, $K^+$ 90, $Ca^{++}$ 86, $Na^+$ 78, and $pO_2$ 70. In one embodiment, the cartridge 37 also incorporates an electrochemical sensor card 50, which includes the sensor assembly 10.

Figure 3:
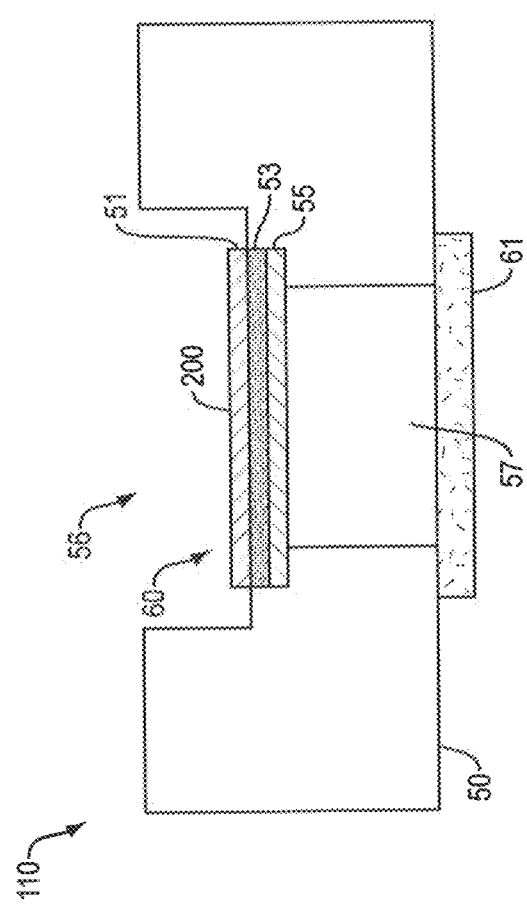
FIG. 3 illustrates a cross-sectional view of the exemplary hemolysis sensor illustrated in FIG. 2, according to an embodiment of the invention.

Referring to FIG. 1, the cartridge 37 contains a sensor card 50 (also known as electrode or support card), illustrated for example in FIGS. 1-3, including the sensor assembly 10 which provides a low volume, gas tight chamber in which the sample, such as a whole blood sample, internal reference solution, or a monomer-containing solution, is presented to one or more electrochemical sensors, e.g., hemolysis sensor 110, pH 94, $pCO_2$ 93, $pO_2$ 70, $Na^+$ 78, $Ca^{++}$ 86, glucose 91, lactate 92, creatine 118, creatinine 116 and hematocrit sensors.

With continued reference to FIG. 1, in one embodiment of the invention, the electrochemical sensor system 8 incorporates in the cartridge 37 at least three prepackaged containers 14, 16, and 17, each containing an internal reference solution having known values of the parameters to be measured by the system 8. Each of the prepackaged containers 14, 16 and 17 contain a sufficient quantity of its internal reference solution to allow the sensors of the sensor assembly in the system 8 to be calibrated a substantial number of times before the prepackaged container 14, 16, 17 becomes empty. When one or more of the containers 14, 16 and 17 containing the internal reference solutions are empty, the cartridge containing prepackaged containers 14, 16 and 17 is replaced.

Referring to FIG. 2, as a blood sample, such as a whole blood sample, or internal reference solution volume introduced into the sensor channel 56 passes through the sensor channel 56 to the output section 34, it passes over a number of sensors, for example, the hemolysis sensor 110, as illustrated in FIG. 2. For example, the blood sample and/or internal reference solution can be passed over the hemolysis sensor 110, a $pO_2$ sensor 70, a $Na^+$ sensor 78, a $Ca^{++}$ sensor 86, a $K^+$ sensor 90, a glucose sensor 91, a lactate sensor 92, a $pCO_2$ sensor 93, a pH sensor 94, hematocrit sensors 98, 100, a creatinine sensor 116, and a creatine sensor 118.

Referring still to FIG. 1, the cartridge 37 also includes a container 28 for a solution surrounding a reference electrode. The container 28 is connected to the sensor assembly 10 by a flow line 30. The system further includes a waste container 32, which receives the blood samples, the internal reference solution and the solution for the reference electrode 28 after they have passed through the sensor assembly 10. In one embodiment, the sensor assembly 10 transmits these samples (e.g., blood samples) to the waste container 32 via a flexible conduit 34. Referring still to FIG. 1, the electrochemical sensor system 8 is formed upon insertion of the cartridge 37 housing the sensor assembly 10 including the hemolysis sensor 110 into the electrochemical sensor system 8. Upon insertion, the sensor assembly 10 fits into a heater block assembly 39.

The sensor assembly 10 may also have a number of edge connectors 36 in a bank which allow it to be plugged into a female matching connector of the electrical interface 38 so that the electrodes formed on the assembly 10 may be connected to a microprocessor 40 through an analog board 45. The microprocessor 40 is connected to the multiport valve 18 via a valve driver 43 by a line 42 and to the motor of the peristaltic pump 26 via a pump driver 45 by a line 44.

Referring to FIG. 2, by way of example, the sensor card 50 in the sensor assembly 10 in one embodiment consists of a structurally rigid rectangular card, such as, polyvinylchloride having, for example, a rectangular aluminum (or other suitable material) cover plate 52 adhered to one of its surfaces. In one embodiment of the invention, cover plate 52 closes off the sensor flow channels 56 which introduce the blood sample to the membranes of the sensors formed in one surface of the card 50 and also acts as a heat transfer medium for hydrating the sensors by thermal cycling and to maintain the fluids flowing through the sensor assembly 10, and the electrodes themselves, at a constant temperature during calibration and during measurement of relevant parameters in a patient whole blood sample. The sample flow channel in one embodiment is devoid of a reagent introduced into the sample, i.e., the chamber is reagentless. This may be achieved by measuring the temperature of the plate 52 and employing a suitable heating or cooling element e.g., a Peltier-effect device and thermistor 41 (FIG. 1) to maintain the temperature of the plate 52 at a desired temperature.

FIG. 3 illustrates the exemplary hemolysis sensor 110 illustrated in FIG. 2 according to one embodiment of the invention. The illustrated hemolysis sensor 110 includes a composite membrane 60 comprising three layers (the terms layer(s) and membrane(s) are interchangeably used herein to represent a membrane), described here beginning with the layer that is in contact with the blood sample, i.e., an outer layer 51 (also referred to as an outer membrane), followed by an intermediate layer 53 (also referred to as an enzyme layer or enzyme membrane) in contact with the outer layer 51 on one side of the intermediate layer 53, and in contact with an inner layer on the opposite side of the intermediate layer, the inner layer 55 (also referred to as inner membrane or an interference rejection layer) described below in greater detail, the inner layer is in contact with the intermediate layer on one side of the inner layer and a working electrode 57 on the other side of the inner layer, the electrode 57 made from a metal, platinum, for example.

The hemolysis sensor is positioned on the floor of the sensor channel 56 which is a channel in the sensor card 50 (FIG. 2). The sensor card 50 provides low volume gas tight flow through chamber in which the patient sample, such as whole blood (e.g., hemolyzed blood), plasma, or serum is presented to the one or more sensors on the card 50 including but not limited to a hemolysis 110 (extracellular hemoglobin), glucose 91, lactate 92, creatine 118, creatinine 116, $pCO_2$ 93, pH 94, $K^+$ 90, $Ca^{++}$ 86, $Na^+$ 78, $pO_2$ 70 sensors. In one embodiment, the hemolysis sensor 110 includes a reference electrode and a counter electrode.

Figure 4:
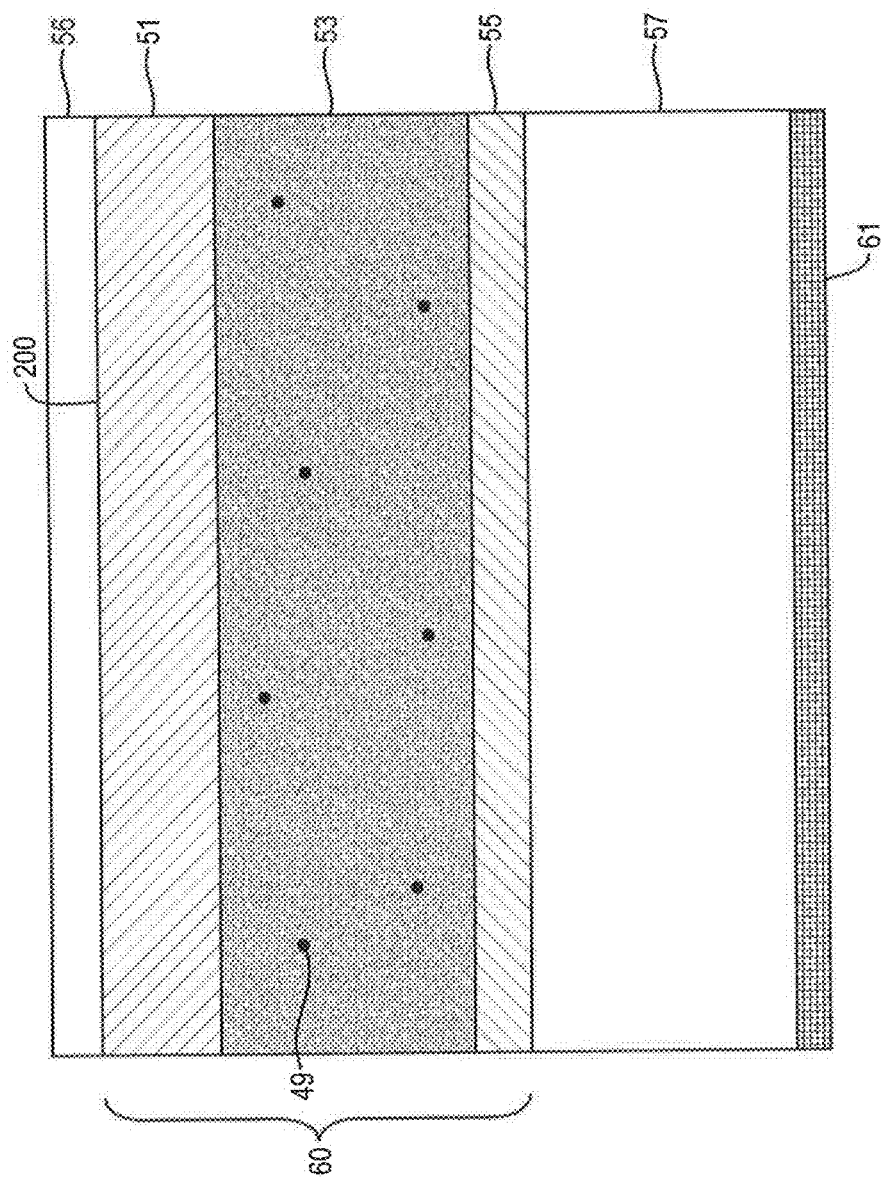
FIG. 4 illustrates another cross-sectional view of the exemplary hemolysis sensor illustrated in FIG. 2 according to an embodiment of the invention.
Figure 5:
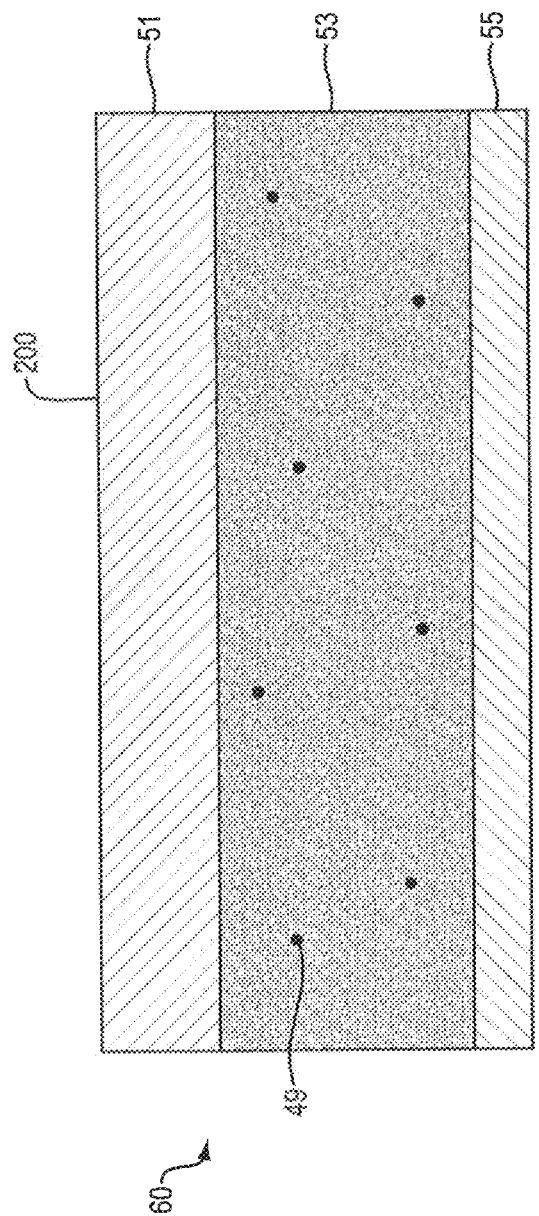
FIG. 5 illustrates a cross-sectional view of the composite layer of the exemplary hemolysis sensor illustrated in FIG. 2 according to an embodiment of the invention.
Figure 6:
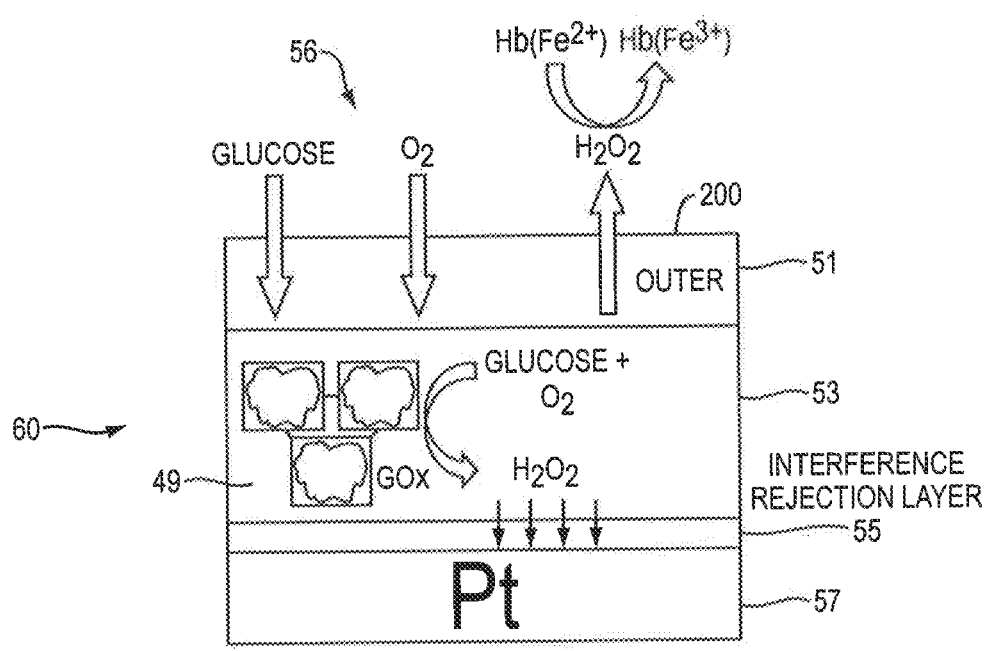
FIG. 6 illustrates another embodiment of the hemolysis sensor with an exemplary glucose oxidase enzyme layer.

Referring now to FIGS. 3-6, the composite membrane 60 of the hemolysis sensor 110 includes a layer 53 which generates $H_2O_2$ via a chemical reaction (e.g., enzymatic reaction). The composite membrane 60 comprises two, three or more membranes (or layers), for example, an outer membrane (or outer layer) 51 positioned in contact with the sensor channel 56, an enzyme membrane (or enzyme layer) 53 comprising an oxidoreductase enzyme, such as glucose oxidase, and an inner interference rejection membrane (or inner interference rejection layer, or inner layer) 55 in contact with a working electrode (FIGS. 4-6).

Outer Layer or Outer Membrane of the Composite Membrane of the Hemolysis Sensor

Referring to FIG. 3, an outer membrane 51 is generally positioned on the surface of the hemolysis sensor 110 in contact with the patient whole blood sample in the sample flow chamber 56. The outer membrane 51 is composed of a polyurethane component, for example but not limited to, an aliphatic polyether polyurethane with about 45-100% water content, which readily permits diffusion of $H_2O_2$ through the outer surface of the outer membrane 51 from within the hemolysis sensor 110 into the blood flow chamber 56 where the $H_2O_2$ mixes with the whole blood sample.

In one embodiment of the invention, the thickness of the outer membrane 51 controls rate of $H_2O_2$ diffusion from the intermediate layer (e.g., the enzyme layer 53, and the inner layer (e.g., interference layer 55), or the working electrode 57 through the outer membrane 51, thus in one embodiment, the thickness of the outer membrane 51 of the hemolysis sensor 110 is selected based on net transfer of $H_2O_2$ across the outer membrane 51, from regions of high $H_2O_2$ concentration (e.g., the enzyme layer 53, other inner layers (e.g., interference layer 55) or the working electrode 57 to low $H_2O_2$ concentration (e.g., the outer membrane 51).

In a conventional glucose 91, lactate 92, creatine 118, creatinine 116 or $pO_2$ 70 sensor, the thickness of the outer membrane used in these sensors is disadvantageous and is inoperative to measure hemolysis because the permeability of the outer membrane in these sensors to $H_2O_2$ is low, as compared to the permeability of the outer membrane to $H_2O_2$ in the hemolysis sensor 110 according to the invention described herein. As a result, the outer membrane of the conventional glucose 91, lactate 92, creatine 118, creatinine 116 or $pO_2$ 70 sensor does not permit $H_2O_2$ diffusion across membranes (i.e., from the inner membranes towards the outer membrane or through the outer membrane to the surface of the membrane) and thus would be inoperative in the hemolysis sensor described herein. As little or no $H_2O_2$ diffuses from the inner membranes to the outer membrane of the conventional glucose 91, lactate 92, creatine 118, creatinine 116 or $pO_2$ 70 sensors, there is no decrease in the $H_2O_2$ availability needed for oxidation at the working electrode, e.g., a platinum electrode, as compared to the hemolysis sensor 110 in which there is a decrease in the $H_2O_2$ availability needed for oxidation at the working electrode because of the increase in hydrogen peroxide permeability that characterizes the permeability of the outer membrane of the hemolysis sensor according to the invention. Therefore, conventional glucose 91, lactate 92, creatine 118, creatinine 116 or $pO_2$ 70 sensor do not provide a sufficient decrease in the amplitude of the current irrespective of whether or not extracellular hemoglobin from whole blood is present, as compared to the hemolysis sensor 110, which provides a sufficient decrease in the amplitude of the current in presence of extracellular hemoglobin from the whole blood.

Additionally, in the conventional glucose 91, lactate 92, creatine 118, creatinine 116 or $pO_2$ 70 sensor, the thickness of the outer membrane used in these sensors is also disadvantageous and inoperative in the hemolysis sensor 110 because the conventional outer membrane (in glucose 91, lactate 92, creatine 118, creatinine 116 or $pO_2$ 70 sensor) is less permeable, as compared to the outer membrane in the hemolysis sensor 110, to substrates (e.g., glucose) required to generate hydrogen peroxide in the hemolysis sensor 110. In the hemolysis sensor, 110, sufficiently more hydrogen peroxide generation, as compared to the hydrogen peroxide generation in the conventional glucose 91, lactate 92, creatine 118, creatinine 116 or $pO_2$ 70 sensor, is necessary for the detection of hemolysis by the hemolysis sensor 110.

Furthermore, the hemolysis sensor 110 having an outer membrane of the conventional glucose 91, lactate 92, creatine 118, creatinine 116 or $pO_2$ 70 sensor is inoperative to measure hemolysis because the thickness of the outer membrane provided by the conventional glucose 91, lactate 92, creatine 118, creatinine 116 or $pO_2$ 70 sensor, if used in the hemolysis sensor 110, generates erroneous results with respect to decrease in the amplitude of the current in the presence of extracellular hemoglobin in the whole blood sample, possibly because of the low permeability of the outer membrane of the conventional glucose 91, lactate 92, creatine 118, creatinine 116 or $pO_2$ 70 sensor to $H_2O_2$.

In one embodiment of the invention, the thickness of the outer membrane 51 of the hemoglobin sensor 110 ranges from about 0.01 μm to about 100 μm, about 0.01 μm to about 90 μm, about 0.1 μm to about 80 μm, about 0.1 μm to about 70 μm, about 0.1 μm to about 60 μm, about 0.1 μm to about 50 m, about 0.1 μm to about 40 μm, about 0.1 μm to about 30 μm, about 0.1 μm to about 20 μm, preferably about 0.1 to about 15 μm, more preferably about 0.1 to about 10 μm.

In an alternative embodiment of the invention, it is contemplated that the outer membrane 51 is not needed and the extracellular hemoglobin in a patient's hemolyzed whole blood sample permeates the enzymatic intermediate layer 53 and directly interacts with $H_2O_2$ in the enzymatic intermediate layer 53 of the hemolysis sensor 110 in the absence of the outer membrane 51.

In one embodiment of the invention, the outer membrane 51 comprises a hydrogel having water content ranging from about 0.1% to about 100% about 0.5% to about 100%, about 1% to about 90%, about 5% to about 80%, about 10% to about 75%, about 20% to about 60%, about 30% to about 50%, preferably about 40% to about 70% more preferably about 60% to about 70%. Also contemplated is an outer membrane 51 according to the invention having water content ranging from 0-5%, 5-10%, 10-15%, 15-20%, 20-30%, 30-40%, 40-50%, 50-60%, 60-70%, 70-80%, 80-90%, or 90-100%.

In one embodiment, according to the invention, the linear expansion, defined as expansion of a hydrogel when it is soaked in water, of the outer membrane 51 of the hemolysis sensor 110 ranges from about 0.1% to about 100%, about 0.5% to about 100%, about 1% to about 100%, about 5% to about 100%, about 10% to about 100%, about 20% to about 100%, about 30% to about 100%, about 40% to about 100%, about 50% to about 100%, about 60% to about 100%, about 70% to about 100%, about 80% to about 100%, about 90% to about 100%, or about 100%, preferably about 15% to about 65%, more preferably about 20% to about 45%.

In one embodiment according to the invention, the outer membrane layer 51 comprises a hydrogel composed of a polyurethane component. For example, the composition of the outer membrane is aliphatic polyether polyurethane with 45-100% water content.

In another embodiment of the hemolysis sensor 110, according to the invention, the viscosity of the outer membrane 51 regulates the thickness of the outer membrane 51. Thickness of membrane controls rate of $H_2O_2$ diffusion across the outer membrane 51. For example, the viscosity of the outer membrane 51 ranges from about 0 centipoise (cps) to about 10,000 cps, about 0 to about 9,000 cps, about 0 to about 8,000 cps, 0 to about 7000 cps, about 0 to about 6000 cps, about 0 to about 5000 cps, about 0 to about 4000 cps, about 0 to about 3,000 cps, about 0 to about 2000 cps, about 0 to about 1000 cps, about 0 to about 900 cps, about 0 to about 800 cps, about 0 to about 700 cps, about 0 to about 600 cps, about 0 to about 500 cps, about 0 to about 400 cps, about 0 to about 300 cps, about 0 to about 200 cps, about 0 to about 100 cps, about 0 to about 90 cps, about 0 to about 80 cps, about 0 to about 70 cps, about 0 to about 60 cps, about 0 to about 50 cps, about 0 to about 40 cps, about 0 to about 30 cps, about 0 to about 20 cps, about 0 to about 10 cps, about 0 to about 1 cps, preferably about 10 cps to about 5000 cps, more preferably about 10 cps to about 2500 cps.

Referring to FIGS. 4 and 5, in yet another embodiment of the invention, the permeability of the outer membrane 51 permits diffusion of $H_2O_2$ by random movement of molecules across different membrane layers in the hemolysis sensor 110, or permits net movement of $H_2O_2$ from regions of high concentration, such as the inner membrane (e.g., enzyme membrane 53) to the outer membrane 51 or alternatively from the outer membrane 51 to the surface 200 of the outer membrane 51 in the hemolysis sensor 110. For example, diffusion of hydrogen peroxide occurs from the enzyme layer 53 or the interference rejection layer 55 or from in and around i.e., in close proximity of the working electrode 57 to the whole blood sample in the channel 56. In another embodiment, the permeability of the outer membrane 51 is not saturated as the $H_2O_2$ concentration or gradient changes, i.e., the outer membrane 51 is not saturated with $H_2O_2$, as the $H_2O_2$ concentration or gradient changes (i.e., increases or decreases) from the enzyme layer 53 or interference rejection layer 55 or in and around i.e., close proximity of the working electrode 57 to the outer surface 200 of the outer layer 51. In another embodiment, the outer membrane 51 is composed of materials (e.g., aliphatic polyether polyurethane) such that diffusion of different constituents in the whole blood or plasma, such as but not limited to, electrolytes, oxygen, hemoglobin, carbon dioxide, bicarbonate, methane, proteins, do not interfere with the diffusion of $H_2O_2$ from the inner membrane (e.g., enzyme membrane 53) towards the outer membrane 51.

The electrical signal output of the hemolysis sensor to monitor or detect hemolysis in whole blood is influenced by the variations in partial oxygen pressure ($pO_2$) that may occur in an individual patient's whole blood sample, for example, a hemolyzed whole blood sample. This is because, this sensor employs an outer hydrogel membrane permeable to oxygen and peroxide formation is dependent on $pO_2$ level. The oxygen partial pressure indicates how much oxygen from the patient's whole blood is available for an enzymatic reaction in the enzyme intermediate layer 53 of the hemolysis sensor 110.

In an exemplary study to determine the influence of $pO_2$ on the hemolysis sensor response it was found that higher $pO_2$ ensures higher response for the same level of substrate, i.e., glucose, compared to lower $pO_2$. For example, in FIG. 10, a $pO_2$ pressure of 203 mmHg in 1% lysed blood indicates greater oxygen availability as compared to a $pO_2$ pressure of 19.8 mmHg in 1% lysed blood. Hence, the sensitivity of the hemolysis sensor 110 to detect hemolysis in whole blood increases with increased $pO_2$ in the patient's whole blood. Thus, according to an embodiment of the invention, the response of the hemolysis sensor to hemolysis in whole blood can be varied by altering the influx of oxygen through the outer membrane 51 of the hemolysis sensor 110.

Figure 9B:
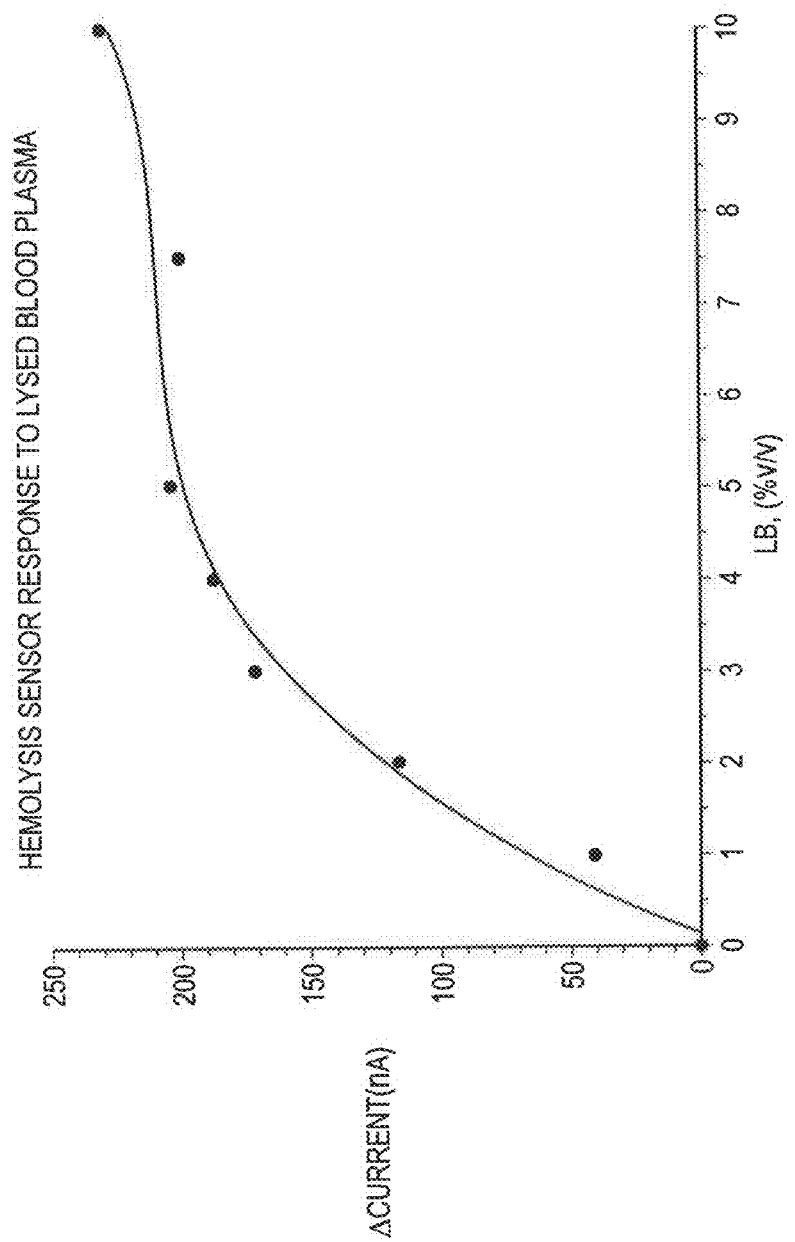
FIG. 9B is a graph illustrating the exemplary hemolysis sensor, shown in FIG. 9A, response to different volume percentages of lysed blood.
Figure 10:
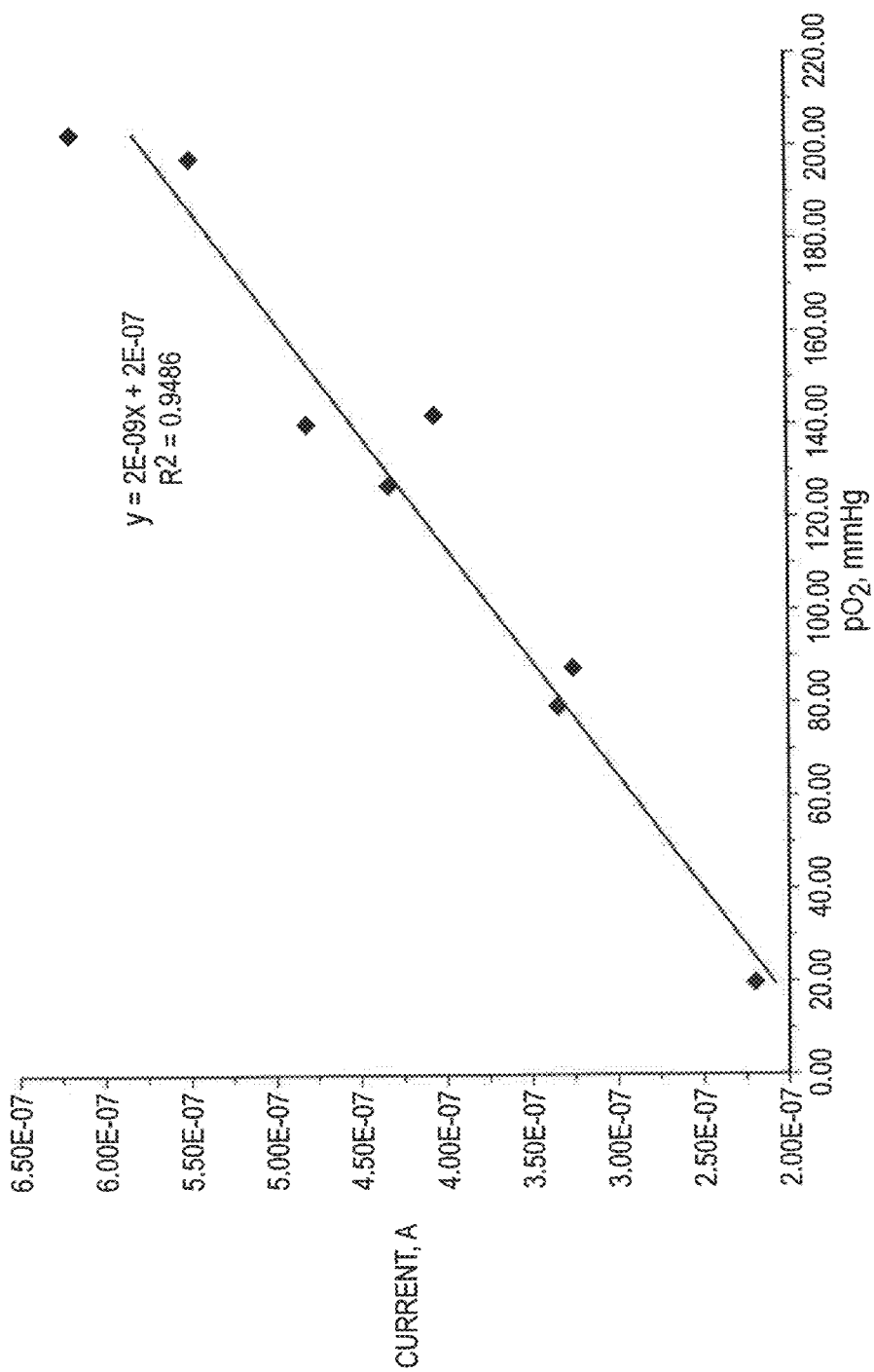
FIG. 10 is a graph illustrating the expected influence of $pO_2$ on the hemolysis sensor response comprising an exemplary glucose oxidase enzyme layer according to the invention.

While, FIG. 10 is illustrative of the influence of whole blood $pO_2$ on sensitivity of the response of the hemolysis sensor 110, it should be noted that at a constant oxygen partial pressure, the current generated at the working electrode 57 of the hemolysis sensor 110 is always lower in the presence of hemoglobin, as compared to the current generated at the working electrode 57 in the absence of hemoglobin (compare current output for 1% lysed blood and whole blood at $pO_2$ of 200 mmHg in FIG. 9A).

In another non-limiting exemplary embodiment of the invention, the outer membrane 51 is produced by dispensing a solution of 20.0 mL tetrahydrofuran solvent, 0.2 g of 59% water uptake polyurethane onto the enzyme layer 53 of the composite membrane 60.

In another embodiment, one or more commercially available membranes, such as D1, D2, D3, D4, D6, D640, D7, and HYDROSLIP, available from AdvanSource Biomaterials (Wilmington, Mass.), are used as outer membrane 51 is encompassed in accordance with the embodiments of the invention. Properties of commercially available outer membranes are shown in Table 2 below.

TABLE 2

Properties of commercially available outer membranes

| | HM D Series | | | | | | | |
|---|---|---|---|---|---|---|---|---|
| | D1 | D2 | D3 | D4 | D6 | D640 | D7 | HydroSlip C |
| % Linear Expansion | 45 | 25 | 40 | 50 | 60 | 100 | 10 | 180 |
| % Water Content | 70 | 55 | 60 | 50 | 80 | 90 | 30 | 95 |
| Viscosity | 2240 cps | 10.2 cps | — | 65.1 cps | — | — | — | — |

The outer membrane 51, which is layered directly onto and in contact with the enzyme layer 53, may also function to preserve the enzyme layer 53 by preventing exposure of an enzyme 49, glucose oxidase, for example, embedded in enzyme layer 53, and the stabilizing matrix in which the enzyme 49 is embedded, to degradatory proteins or compounds from the sample in channel 56. Likewise, outer membrane 51 may prevent diffusion of the enzyme 49 out of the enzyme layer 53. The outer membrane 51 may also function to control the rate of diffusion of substrate (e.g. glucose, lactate, creatine and creatinine) and oxygen from the sample to the enzyme layer 53, as discussed above. Referring still to FIGS. 3 and 4, in an embodiment, the outer membrane 51 of the hemolysis sensor 110 generally functions to control or regulate the diffusion of $H_2O_2$ from the enzyme layer 53. The outer membrane 51 may also protect the other components of hemolysis sensor 110 from direct contact with constituents of the sample in channel 56. In one embodiment, the outer membrane 51 is a polymeric membrane comprising one or more polyurethane-based compounds. The hydrophilicity or the hydrophobicity of the membrane is determined by the mixture of species of polymer compounds. For example, if the hydrophilicity of the membrane is increased, it may facilitate or expedite the ability of $H_2O_2$ to diffuse through the membrane more rapidly. The optimal composition of the outer membrane 51 is the concentration in which an optimal balance of diffusion rates of $H_2O_2$, exists under typical conditions.

Referring to FIG. 4, the outer membrane 51 provides a means for a hemolyzed sample (e.g., whole blood) to come in contact with $H_2O_2$, generally diffusing from the enzyme layer. In an exemplary embodiment, when a hemolyzed sample is placed on the outer surface 200 of the outer layer 51, the hemoglobin content released from the hemolyzed sample scavenges $H_2O_2$ diffusing from the enzyme layer 53 to the outer layer 51.

In an embodiment, the outer membrane 51, which is layered directly onto and in contact with the enzyme layer 53, may also function to preserve the enzyme layer 53 by preventing exposure of an enzyme 49 embedded in enzyme layer 53, and the stabilizing matrix in which the enzyme 49 is embedded, to degradatory proteins or compounds present in the patient blood sample in channel 56. Likewise, outer membrane 51 may prevent diffusion of the enzyme 49 out of the enzyme layer 53. The outer membrane 51 also functions to control the rate of diffusion of substrate (e.g. glucose, lactate, creatine and creatinine) and oxygen from the sample to the enzyme layer 53.

In one embodiment, when there is no outer membrane, the enzyme layer 51, discussed below in greater detail, contacts the sample as the sample flows along the sensor channel 56 and over the hemolysis sensor 110. The electrical signal generated by the oxidation of hydrogen peroxide at the working electrode 57 is carried by a platinum wire in the working electrode 57 and transferred to the conductor 61 which is in electrical communication with the electrical interface 38 and contacts 36 shown in FIG. 1.

Intermediate Layer or Intermediate Membrane (Enzyme Layer) of the Hemolysis Sensor Referring still to FIG. 4, the enzyme layer 53 of the hemolysis sensor 110 includes at least one enzyme 49 that is stabilized in the matrix of the enzyme layer 53. The enzyme 49 is required for the enzymatic reaction in which a specific substrate participates. In one embodiment, the enzyme 49 includes at least one protein with enzymatic activity. In other embodiments, enzyme 49 includes a mixture of several enzymes, proteins and stabilizers, for example.

In an exemplary embodiment of the invention, the protein enzyme 49 is glucose oxidase, lactate oxidase, or a mixture of enzymes (e.g., creatininase, and/or creatinase and sarcosine oxidase) which are embedded in the enzyme layer 53 of the hemolysis sensor 110. The hemolysis sensor 110 is an $H_2O_2$ generator, i.e., hemolysis sensor 110 generates $H_2O_2$ when the enzyme 49 in the enzyme layer 53 is contacted with the enzyme substrate. In an exemplary embodiment, the hemolysis sensor 110 includes glutaraldehyde and glucose oxidase in the enzyme layer 53. In one embodiment, the hemolysis sensor 110 includes 0.10 g of glutaraldehyde per gram of glucose oxidase. In another exemplary embodiment, the hemolysis sensor 110 includes at least glutaraldehyde, bovine serum albumin, and an enzyme stabilizer such as, for example, polyethyleneimine and lactate oxidase in the enzyme layer 53. In one embodiment, the hemolysis sensor 110 includes 45% lactate oxidase by weight, 45% bovine serum albumin by weight, 5% polyethylenimine (an enzyme stabilizer) by weight and 5% glutaraldehyde by weight, for example. The weight fractions of lactate oxidase and bovine serum albumin can vary. The weight percent of polyethylenimine in the enzyme layer can vary, and the weight percent of glutaraldehyde can vary. Other enzymes stabilizers include but are not limited to polyionic compounds such as polypropyleneimine, poly(N-vinylimidazole), polyallylamine, polyvinylpiridine, polyvinylpyrollidone, polylysine, protamine and their derivatives.

In yet another embodiment of the invention, enzyme layer 53 of the hemolysis sensor 110 includes a mixture of several enzymes, proteins, and stabilizers embedded in the matrix of enzyme layer 53 for specific production of $H_2O_2$ using a glucose oxidase or a lactate oxidase, only hemolysis sensor 110.

Enzyme mixtures are used in the hemolysis sensor 110 to generate $H_2O_2$, which is scavenged by hemoglobin from hemolyzed whole blood. In an exemplary embodiment of the invention, the hemolysis sensor 110 includes a mixture of 5% creatininase by weight, 55% creatinase by weight, 30% sarcosine oxidase by weight, 5% poly(N-vinylimidazole) (an enzyme stabilizer) by weight and 5% glutaraldehyde by weight, for example.

The weight fractions of creatininase, creatinase and sarcosine oxidase in the hemolysis sensor 110 and the weight fractions of creatinase and sarcosine oxidase in the hemolysis sensor 110 can vary. The weight percent of poly(N-vinylimidazole) in the hemolysis sensor 110 can vary, for example, from 1% to 20%, and the weight percent of glutaraldehyde in the creatinine and creatine electrodes can also vary, for example, from 1% to 10%. Polyionic stabilizers, other than poly(N-vinylimidazole), can also be used for stabilizing the enzyme mixture. Examples of polyionic compounds include but are not limited to polyethylenimine, polypropyleneimine, polyallylamine, polyvinylpiridine, polyvinylpyrollidone, polylysine, protamine, and their derivatives.

In one embodiment, the enzyme layer 53 of the hemolysis sensor comprising a glucose oxidase, a lactate oxidase, a mixture of enzymes (e.g., creatininase and/or creatinase and sarcosine oxidase) consists of a cross-linked matrix of enzymes, stabilizers such as polyethylenimine or poly(N-vinylimidazole), and other proteins such as bovine serum albumin. Cross-linking of the enzymes, stabilizers, and other protein molecules is accomplished with, for example, glutaraldehyde, and a dialdehyde. Other cross-linking reagents, such as 1,4-diisocyanatobutane, a diisocyanato, 1,2,7,8-diepoxyoctane and 1,2,9,10-diepoxydecane, both diepoxides, can also be used. Cross-linking of the enzyme molecules and the use of the polyionic stabilizers and inert proteins in the enzyme matrix can significantly extend the shelf-life and the use-life of the enzyme electrodes.

Inner Layer or Inner Membrane (Interference Rejection Membrane)

Referring to FIGS. 3 and 4, the hemolysis sensor 110 also includes an inner interference rejection membrane or layer 55 which is a restorable polymeric membrane in close contact to the working electrode 57 having a conducting platinum wire. The inner interference rejection membrane 55 is formed by the polymerization of electropolymerizable monomers into an inner polymeric membrane on the hemolysis sensor 110. Suitable electropolymerizable monomers include benzothiophene, phenylenediamines (e.g., m-phenylenediamine (PDA), and phenols, for example). The inner interference rejection membrane 55 insulates or protects the wire in the working electrode 57 from compounds in the sample, specifically oxidizable compounds, which interfere with the proper functioning of the hemolysis sensor 110. In one embodiment, the interference rejection membrane is permeable only to $H_2O_2$ and blocks larger molecules from undergoing oxidation on the working electrode 57, thereby ensuring that current response arises only from $H_2O_2$.

Other metal such as gold, carbon, silver, copper, palladium and iridium can be substituted for the platinum at the working electrode 57.

In one embodiment according to the invention, the polymeric membrane comprising the inner interference rejection membrane 55 is formed by the application of an electrical potential to the working electrode 57 comprising a conductive wire (e.g., a platinum wire) in the presence of electropolymerizable monomers. The monomers in the presence of an electrical potential polymerize on the working electrode 57 to form an electrically insulating polymeric inner interference rejection membrane 55 on the working electrode 57 illustrated in FIGS. 3 and 4. Hydrogen peroxide, which is generated from activity of the enzyme in the enzyme layer 53 of the hemolysis sensor 110 on a specific substrate, passes through the pores of the inner interference rejection membrane 55 and contacts the working electrode 57 causing an electrical signal to be generated at the working electrode 57. The smaller size of the pores in the inner interference rejection membrane 55 restricts compounds found in the sample, larger than hydrogen peroxide, such as acetaminophen, ascorbic acid, uric acid, cysteine and other electroactive compounds (generally referred to as interfering substances) that are larger than $H_2O_2$ from producing a false signal and reducing accuracy of the hemolysis sensor.

EXEMPLIFICATION

The hemolysis sensor 110 described above can be adapted for use in commercially available electrochemical sensor systems, such as GEM 4000 (Instrumentation Laboratory Company, Bedford, Mass.). As an example, a hemolysis sensor was prepared as follows: enzyme, glucose oxidase (GOx), solution was prepared in 50 mM phosphate buffer, pH 7.2, at a GOx concentration ranging from 0.1 to 50 mg/ml. GOx was allowed to cross-link with glutaraldehyde solution (0.06 to 6%). The cross-linked enzyme solution was drop casted on a platinum electrode surface and air-dried for 30 minutes. Similarly, an outer membrane hydrogel D2 (AdvanSource Biomaterials, Wilmington, Mass.) (1%) in tetrahydrofuran (THF) was drop casted on to the enzyme layer and air-dried for 30 minutes. After drying, the modified platinum electrode was hydrated in GEM 4000 Cal B buffer solution (Instrumentation Laboratory Company, Bedford, Mass.), pH 7.4 solution for 90 minutes at room temperature for use in a GEM 4000 clinical analyzer (Instrumentation Laboratory Company, Bedford, Mass.).

In another aspect, the invention is directed to methods for detecting or monitoring hemolysis of whole blood. In one embodiment of the method, a whole blood sample is introduced to the hemolysis sensor 110 according to the invention having at least one oxidoreductase enzyme in the enzyme layer 53 and an outer membrane 51 that is highly permeable to hydrogen peroxide, followed by detecting an electrochemical signal generated by hydrogen peroxide in the presence of $Hb(Fe^{2+})$. A decrease of detectable current in the range of 4% to 50% from the whole blood baseline at a working electrode 57, is indicative of the presence of hemolysis in the whole blood sample.

As discussed above, hemolysis in whole blood results in increase of intracellular analytes (e.g., such as potassium, magnesium or creatinine) into the fluid (such as plasma), non-cellular portion of the whole blood sample because these analytes, (potassium, magnesium or creatinine) are released from the intracellular contents of ruptured or abnormally permeable red blood cells. Hemolysis produced by disruption of red blood cells during sample collection and handling is a common cause of hemolysis in clinical practice. For example, hemolysis in whole blood is particularly problematic for analysis of potassium because of ~20-fold elevated $K^+$ levels inside red blood cells compared to potassium concentration in plasma ($K^+$—105 mmol/L in red blood cells vs. 4.0 mmol/L in plasma).

For example, hemolysis of about 1% compared to non-hemolyzed whole blood sample will spuriously elevate whole blood $K^+$ by about 0.5 mmol/L, which would be sufficient to be considered clinically relevant in the absence of hemolysis. Therefore, in one aspect, the invention is directed to a method for assessing whether the source of an elevated analyte, such as potassium, in a whole blood sample of a patient is due to an artifact introduced by artifactual hemolysis of the whole blood sample or due to a physiological abnormality in the patient.

Another aspect of the invention relates to a method of detecting or monitoring levels of at least one component in a whole blood sample undergoing hemolysis utilizing the hemolysis sensor 110 of the present invention. The at least one such component in the whole blood that can be monitored to detect hemolysis in whole blood is hemoglobin. However, other blood components in the whole blood, such as, electrolytes, minerals, gases and the like, could also be detected or monitored in conjunction with hemoglobin or could be detected or monitored independent of hemoglobin utilizing the methods of this invention. In a certain aspect, at least one blood component is hemoglobin, which chemically behaves like a peroxidase by virtue of the heme group. Thus in one aspect, the methods of the present invention exploits the peroxides or peroxidase-like activity of a blood component in whole blood to detect or monitor hemolysis.

In one aspect, the electrochemical system 8 (FIG. 1) is configured to detect or monitor hemolysis in whole blood by measuring changes in electrical output of the hemolysis sensor 110. In this aspect, the hemolysis sensor 110 of the electrochemical sensor system 8 detects hemolysis in the sample (e.g., whole blood) by measuring fluctuation in current in the hemolysis sensor 110 induced by hemoglobin as the hemoglobin (a peroxidase) reacts with hydrogen peroxide in the hemolysis sensor 110. As a result of the interaction between hemoglobin and hydrogen peroxide in the hemolysis sensor 110, hydrogen peroxide is decomposed to hydroxyl radicals or to water and oxygen. As a result, less hydrogen peroxide is available for oxidation at the working electrode 57 (e.g., a platinum electrode) of the hemolysis sensor 110, as compared to the availability of hydrogen peroxide in absence of hemoglobin in the hemolysis sensor 110. Oxidation of hydrogen peroxide at the working electrode 57 of the hemolysis sensor 110 generates the electric current in the hemolysis sensor 110. It is important to note that only extracellular hemoglobin (outside the red blood cells) in plasma or serum reacts with hydrogen peroxide and produces signal for hemolysis. Intracellular hemoglobin has no effect on the hemolysis sensor.

In the methods of monitoring or detecting hemolysis by a hemolysis sensor 110 in an electrochemical system 8, the hemolysis sensor 110 of the present invention comprises one or more oxidoreductase enzymes, which produce hydrogen peroxide in presence of a sample and an oxidizing agent.

Hemolysis Sensor with a Glucose Oxidase

Referring to FIGS. 2 and 6, the hemolysis sensor 110, with a glucose oxidase in the enzyme layer 53, functions by scavenging hydrogen peroxide produced by an enzymatic reaction in the enzyme layer 53. The enzyme, glucose oxidase, specifically oxidizes glucose in the presence of an oxidizing agent, oxygen and produces hydrogen peroxide, a compound scavenged by hemoglobin. In the hemolysis sensor 110 the electrochemical signal that is generated by hydrogen peroxide is diminished in the presence of Hb ($Fe^{2+}$).

Hemolysis Sensor with Creatininase and/or Creatinase and Sarcosine Oxidase.

Referring to FIG. 2, a hemolysis sensor with creatininase and/or creatinase with sarcosine oxidase in the enzyme layer, function by detection of hydrogen peroxide produced by enzymatic reaction in their respective enzyme layers. In the embodiment having creatininase, the enzyme layer 53 in the hemolysis sensor 110 includes a mixture of three enzymes: creatininase, creatinase and sarcosine oxidase. This enzyme mixture specifically oxidizes creatinine and creatine and, in the presence of sarcosine oxidase, produces hydrogen peroxide. Hydrogen peroxide is scavenged by hemoglobin. In the hemolysis sensor 110 the electrochemical signal that is generated by hydrogen peroxide is diminished in the presence of Hb ($Fe^{2+}$).

In the embodiment having creatinase, the enzyme layer 53 in the hemolysis sensor 110 includes a mixture of two enzymes: creatinase and sarcosine oxidase. This enzyme mixture specifically oxidizes only creatine and produces hydrogen peroxide. Hydrogen peroxide is scavenged by hemoglobin. In the hemolysis sensor 110 the electrochemical signal that is generated by hydrogen peroxide is diminished in the presence of Hb ($Fe^{2+}$).

Hemolysis Sensor with Lactate Oxidase

Referring to FIG. 2, a hemolysis sensor with lactate oxidase in the enzyme layer 53 functions by scavenging hydrogen peroxide produced by an enzymatic reaction of lactate oxidase on lactate in the enzyme layer 53. The lactate oxidase present in the enzyme layer 53 oxidizes the lactate to produce hydrogen peroxide, which is scavenged by hemoglobin. In the hemolysis sensor 110 electrochemical signal is generated by hydrogen peroxide in the presence of Hb ($Fe^{2+}$).

$H_2O_2$ Scavenging by Hemoglobin

Figure 7:
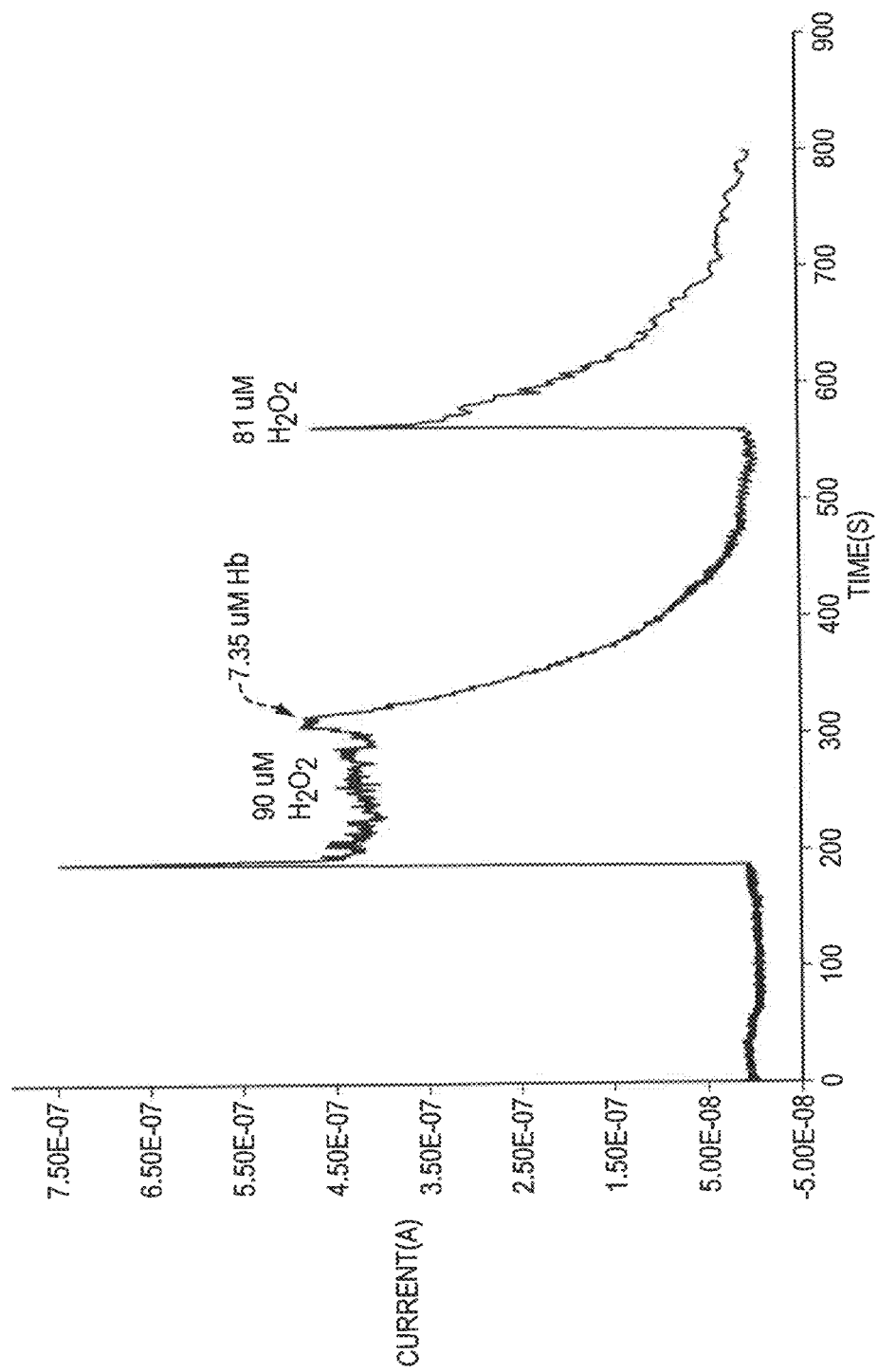
FIG. 7 is a graph illustrating the peroxidase like activity of hemoglobin in a hemolysis sensor comprising an exemplary glucose oxidase enzyme layer according to the invention.

FIG. 7 shows the results of a study directed to the principle of $H_2O_2$ scavenging by hemoglobin. Briefly, a 3-electrode electrochemical cell consisting of a platinum working electrode, a gold counter electrode and a Ag/AgCl, 1 M KCl reference electrode was immersed in a buffer solution (pH 7.4). The working electrode was polarized at +500 mV (vs. Ag/AgCl, 1 M KCl) and its current response was monitored continuously under stirring conditions. Around 180 seconds, $H_2O_2$ (final concentration—90 µM) was injected into the cell, which produces a rise in current response and then stabilized immediately (note: spike observed at 180 seconds was an artifact because of solution injection). This current response arose from the direct oxidation of $H_2O_2$ at the platinum electrode.

With continued reference to FIG. 7, when hemoglobin (final concentration—7.35 µM) was added to the above solution at 320 seconds, a rapid decrease followed by a gradual decrease to the initial background current was observed. This demonstrates that hemoglobin added to the solution caused an immediate decay in current likely caused by the decomposition of hydrogen peroxide in the solution. As the concentration of $H_2O_2$ in the solution decreases, the corresponding current response at the platinum electrode also decreases. A second addition of $H_2O_2$ (final concentration—81 µM) at 550 seconds shows a current spike followed by similar decay in current profile. Such behavior proves that interaction of hemoglobin and $H_2O_2$ in the solution is detectable using electrochemical oxidation at the platinum electrode.

GOx/D2 (1%) Response to Hemolyzed Blood Plasma

FIGS. 8 A and B show the results of a study directed to GOx/D2 (1%) response to hemolyzed blood plasma. In this study, a hemolysis sensor was constructed as follows. Briefly, enzyme GOx solution was prepared in 50 mM phosphate buffer, pH 7.2. The concentration of GOx can range from 0.1 to 50 mg/ml. Glutaraldehyde solution (0.06 to 6%) was added to the above enzyme solution and allowed to cross-link for 30 minutes. The cross-linked enzyme solution was drop casted on the platinum electrode surface and air-dried for 30 minutes. Similarly, outer membrane hydrogel D2 (AdvanSource Biomaterials) (1%) in THF was drop casted on to the enzyme layer and air-dried for 30 minutes. After drying, the modified platinum electrode was hydrated in GEM 4000 Cal B buffer solution (Instrumentation Laboratory Company, Bedford, Mass.), pH 7.4 solution for 90 minutes at room temperature.

Referring to FIGS. 8 A and B, hemolysed analyte samples were prepared as follows. Four 5 mL blood samples from donors were pooled and six 3 mL aliquots were prepared in a plastic tube. The first aliquot was centrifuged and plasma separated. Hemolysis on other five aliquots was caused by forcing the whole blood through a 21-G needle to closely mimic an actual clinical setting collection process. Each back and forth draws constitute a one-syringe draw. The number of times a sample was passed through a needle increased with each subsequent aliquot to produce increasing quantities of hemolysis. After hemolysis, all five aliquots were centrifuged and plasma separated. The glucose concentrations of plasma (1.2 mL) were adjusted to 500 mg/dL.

Figure 8A:
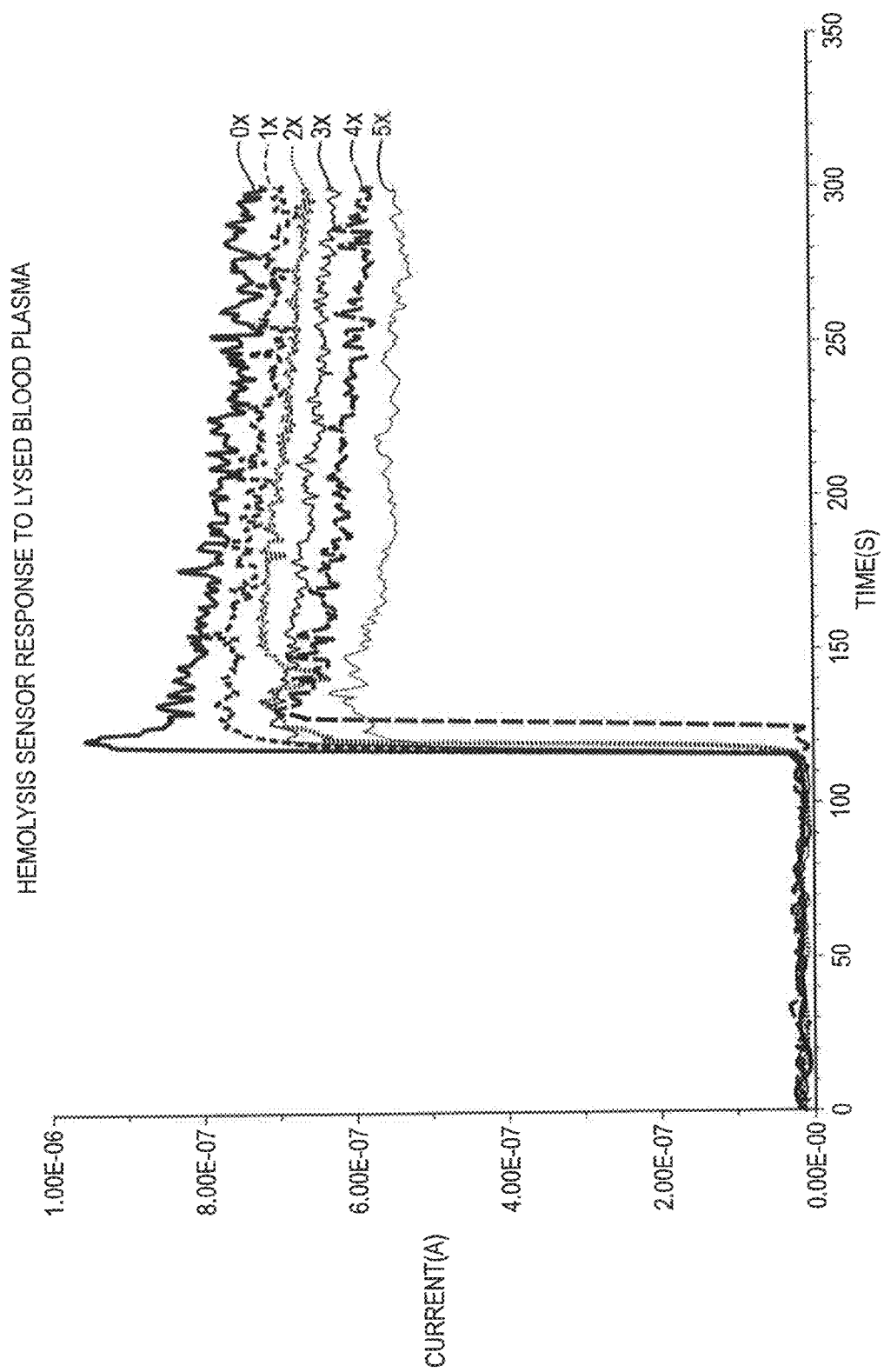
FIG. 8A is a graph illustrating the response of an exemplary hemolysis sensor having a glucose oxidase enzyme layer according to an embodiment of the invention to lysed blood plasma.

With continued reference to FIGS. 8 A and B, the measurements were made in a 3-electrode cell setup as described FIG. 7. Here, a platinum electrode modified with GOx enzyme and a hydrogel membrane acted as working electrode. The cell containing 2400 µL of Cal B buffer solution was stirred continuously and individual aliquots of plasma samples (600 µL) were injected at 120 seconds. FIG. 8A shows the corresponding real-time current responses for each aliquot. Immediately after each injection, hemoglobin and K⁺ values of the plasma aliquot were obtained, which are shown in Table 3 below.

TABLE 3

| syringe draw | tHb, g/dL | K$^+$, mmol/L |
|---|---|---|
| 0 | 0.03 | 4.2 |
| 1 | 0.04 | 4.2 |
| 2 | 0.09 | 4.3 |
| 3 | 0.15 | 4.5 |
| 4 | 0.26 | 4.9 |
| 5 | 0.28 | 5.0 |

Figure 8B:
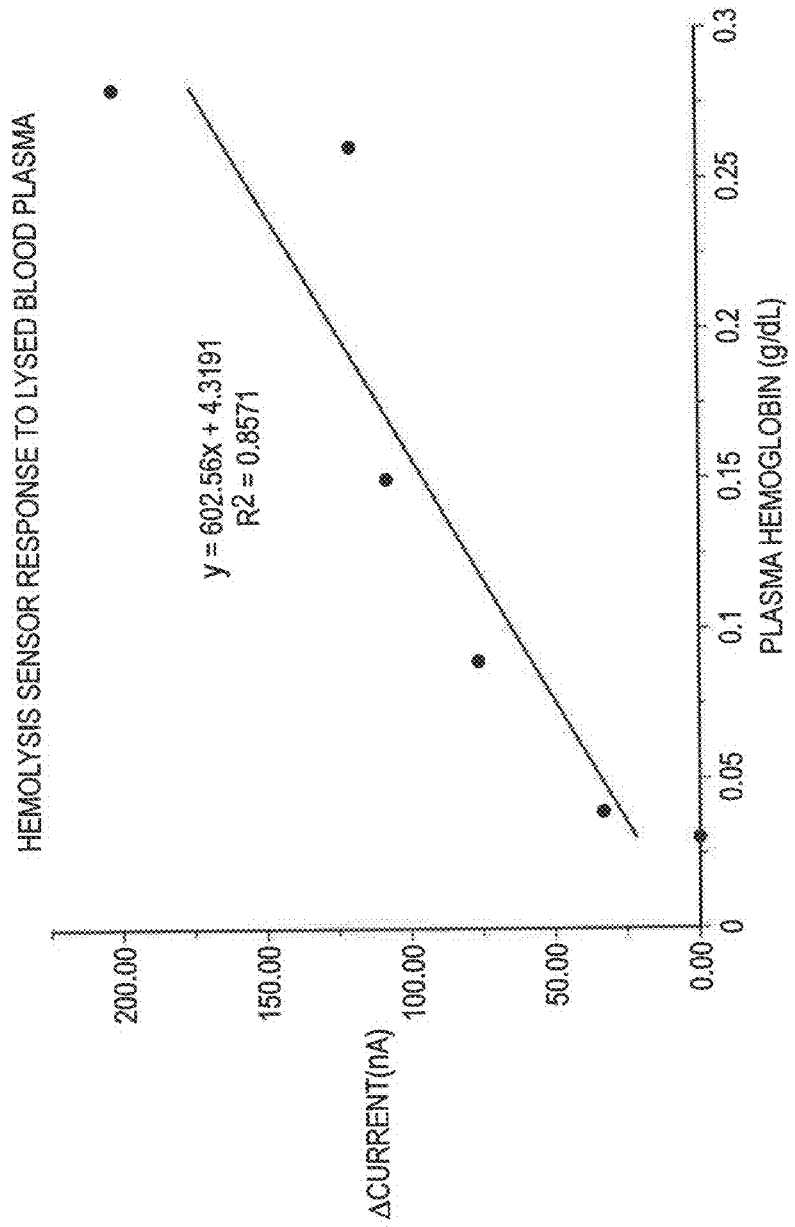
FIG. 8B is a graph illustrating that the response of the hemolysis sensor shown in FIG. 8A to lysed blood plasma is linear.

A hemolysis response calibration graph, FIG. 8B, was constructed by subtracting current response of the hemolyzed samples (1 to 5) from the plasma response with no hemolysis (i.e., 0 syringe draw, see Table 3 above). For this purpose, the current response 30 s after injection was used for calculating the difference between hemolyzed and non-hemolyzed samples. FIGS. 8 A and B clearly demonstrate the above sensor responds immediately to extracellular hemoglobin in the plasma and the response is linear to the hemoglobin concentration.

GOx/D2 (1%) Response to Hemolyzed Blood.

Figure 9C:
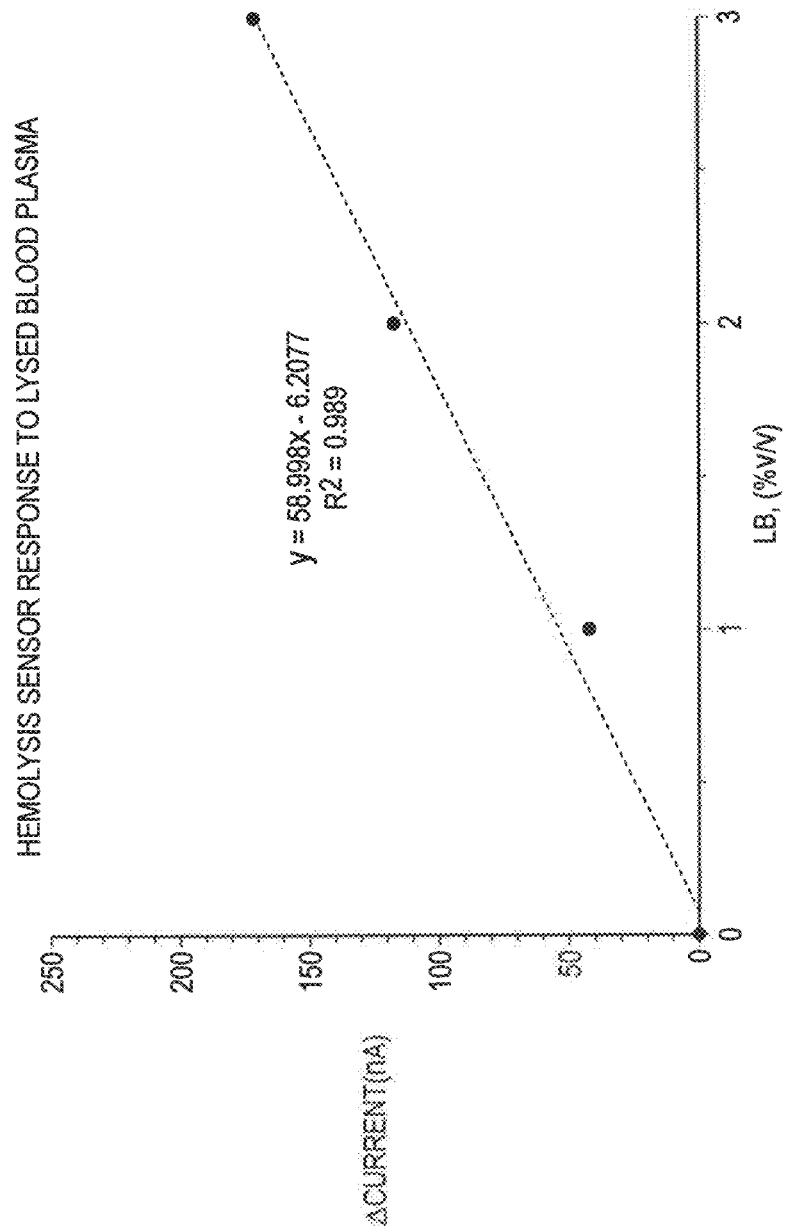
FIG. 9C is a graph illustrating the linear part of the calibration graph generated by the hemolysis sensor of FIGS. 9A and 9B comprising an exemplary glucose oxidase enzyme layer.

The experimental design for the study results of which are shown in FIGS. 9A, 9B and 9C was the same as described above for the study reflected in for FIG. 8, except the sample tested were whole and hemolyzed blood instead of plasma samples. Here, the fractional hemolyzed blood was prepared as % (v/v) solution from an aliquot of completely hemolyzed blood. For example, 1% lysed blood (LB) was prepared by adding 10 µL of lysed blood to 990 µL of whole blood. The glucose levels in all samples were adjusted to a constant value of 500 mg/dL as before.

FIG. 9A shows the real-time current profile for the whole and hemolyzed blood samples while 9B corresponds to the calibration graph calculated. FIG. 9C shows the linear part of the calibration graph. These results illustrate that the hemolysis sensor according to the invention is sensitive and responds to 1%-lysed blood or even lower concentration of lysed blood. It is important to note that the matrix was whole blood and the hemolysis sensor responds only to the extracellular hemoglobin. Such rapid (within 30 s) and sensitive responses are necessary as one of the purpose for this hemolysis sensor is to flag any spuriously elevated K⁺ values in clinical analyzers.

Oxygen Partial Pressure (pO$_2$) Effect on 1% Lysed Blood Detection

With reference to FIG. 10, the pO$_2$ study was carried out to understand the impact of oxygen partial pressure (pO$_2$) on the hemolysis sensor response. As this technology focuses on measuring hemolysis in the patient whole blood, the sample pO$_2$ can vary widely depending on the patient history. On the other hand, hemolysis sensor primarily works by producing H$_2$O$_2$ from glucose and oxygen in the presence of glucose oxidase. The oxygen partial pressure shows how much oxygen is available for this reaction. Higher pO$_2$ ensures higher response for the same level of glucose compared to lower pO$_2$.

FIG. 10 graphically illustrates an expected influence of pO$_2$ on the hemolysis sensor response. The influence of pO$_2$ on the hemolysis sensor response is because the sensor employs an outer hydrogel membrane permeable to oxygen and peroxide formation is dependent on pO$_2$ level. The hemolysis sensor is susceptible to pO$_2$ variations in the patient blood samples because of the membrane permeability to this gas. As demonstrated by this study, the hemolysis sensor according to the invention has a linear negative bias with pO$_2$. For example, pO$_2$ from 200 to 20 mmHg has a linear negative bias for 1% lysed blood, and hence a correction is required to account for such behavior. The correction is done through a response algorithm to account for the pO$_2$ variations.

What is claimed is:

1. A method for detecting hemolysis in a whole blood sample, comprising:
   (i) introducing said whole blood sample to an electrochemical sensor, said electrochemical sensor comprising an oxidoreductase enzyme capable of generating hydrogen peroxide and a hydrophilic outer membrane comprising a thickness in a range of about 0.1 µm to about 50 µm, said membrane thickness adapted to enhance efflux of said hydrogen peroxide, followed by;
   (ii) detecting an electrochemical signal generated by said hydrogen peroxide in the presence of hemoglobin (Hb (Fe$^{2+}$)), wherein a decrease of the electrochemical signal in a range of about 4% to about 50% as compared to a standard non-hemolyzed whole blood sample, is indicative of said hemolysis in the whole blood sample.

2. The method of claim 1 wherein the oxidoreductase enzyme comprises a glucose oxidase.

3. The method of claim 1 wherein the oxidoreductase enzyme comprises a lactate oxidase.

4. The method of claim 1 wherein, the oxidoreductase enzyme is a creatininase.

5. The method of claim 1 wherein the current generated at the working electrode is lower in the presence of said hemoglobin ($Hb(Fe^{2+})$) as compared to the current generated in the absence of said hemoglobin ($Hb(Fe^{2+})$).

6. A method for determining whether an elevated level of an analyte in a whole blood sample of a patient is an artifact related to hemolysis comprising:
   introducing said whole blood sample to an electrochemical sensor, said electrochemical sensor comprising an oxidoreductase enzyme capable of generating hydrogen peroxide and a hydrophilic outer membrane comprising a thickness in a range of about 0.1 μm to about 50 μm, said membrane thickness adapted to enhance efflux of said hydrogen peroxide, followed by;
   detecting an electrochemical signal generated by said hydrogen peroxide in the presence of hemoglobin (Hb($Fe^{2+}$)),
   wherein a decrease of the electrochemical signal in a range of about 4% to about 50% as compared to a standard nor whole blood sample, is indicative of said hemolysis as the cause of the elevated level of the analyte in the whole blood sample of the patient.

7. The method of claim 1 wherein the electrochemical signal is a detectable electrical current.

8. The method of claim 1 wherein said outer hydrophilic membrane comprises a hydrogel.

9. The method of claim 8 wherein the hydrogel comprises water content ranging from about 0.1% to about 100%.

10. The method of claim 6 wherein said outer membrane is composed of a polyurethane component.

11. The method of claim 9 wherein said polyurethane comprises aliphatic polyether.

12. The method of claim 11 wherein said aliphatic polyether polyurethane comprises about 45-100% water content.

13. The method of claim 1 wherein said outer membrane is layered directly onto and in contact with an enzyme layer.

14. The method of claim 13 wherein said enzyme layer comprises at least one enzyme that is stabilized in a matrix of the enzyme layer.

15. The method of claim 1 wherein the oxidoreductase enzyme is a creatinase.

16. The method of claim 1 wherein the oxidoreductase enzyme is a sarcosine oxidase.

* * * * *

UNITED STATES PATENT AND TRADEMARK OFFICE
CERTIFICATE OF CORRECTION

PATENT NO. : 9,658,181 B2
APPLICATION NO. : 14/202398
DATED : May 23, 2017
INVENTOR(S) : Shankar Balasubramian et al.

It is certified that error appears in the above-identified patent and that said Letters Patent is hereby corrected as shown below:

In Column 19, Line 26, Claim 6, please replace --nor-- with --non-hemolyzed--

Signed and Sealed this
Eighth Day of August, 2017

Joseph Matal
*Performing the Functions and Duties of the*
*Under Secretary of Commerce for Intellectual Property and*
*Director of the United States Patent and Trademark Office*